United States Patent [19]
Sorge et al.

[11] Patent Number: 5,858,731
[45] Date of Patent: Jan. 12, 1999

[54] OLIGONUCLEOTIDE LIBRARIES USEFUL FOR PRODUCING PRIMERS

[75] Inventors: Joseph A. Sorge, San Diego; Daniel Davis Shoemaker, Stanford, both of Calif.

[73] Assignee: Stratagene, La Jolla, Calif.

[21] Appl. No.: 313,232

[22] Filed: Feb. 20, 1996

Related U.S. Application Data

[63] Continuation-in-part of Ser. No. 863,412, Apr. 3, 1992, abandoned, Ser. No. 765,694, Sep. 25, 1991, abandoned, and Ser. No. 697,936, May 8, 1991, Pat. No. 5,599,921.

[51] Int. Cl.$^6$ .............................. C12P 19/34; C07H 21/04
[52] U.S. Cl. .................. 435/91.1; 536/24.3; 536/24.33; 536/25.3
[58] Field of Search ................... 435/91.1, 810; 536/24.3, 24.33, 25.3

[56] References Cited

U.S. PATENT DOCUMENTS

| | | | |
|---|---|---|---|
| 5,114,839 | 5/1992 | Blocker | 435/6 |
| 5,366,882 | 11/1994 | Lunnen et al. | 435/199 |
| 5,371,006 | 12/1994 | Morgan et al. | 435/194 |
| 5,599,921 | 2/1997 | Sorge et al. | 536/24.33 |
| 5,663,062 | 9/1997 | Sorge et al. | 435/91.1 |

FOREIGN PATENT DOCUMENTS

WO 89/11211   5/1989   WIPO .

OTHER PUBLICATIONS

Studier. "A Strategy for High–Volume Sequencing of Cosmid DNAs: Random and directed Priming with a Library of Oligonucleotides". *Proceedings of the National Academy of Sciences USA* 86: 6917–6922 (1989).

Szbalski. "Proposal for Sequencing DNA Using Litigation of Hexamers to Generate Sequential Elongation Primers". *Gene* 90: 177–178 (1990).

*Primary Examiner*—Kenneth R. Horlick
*Attorney, Agent, or Firm*—Pennie & Edmonds LLP

[57] ABSTRACT

An oligonucleotide library is described that is1 useful for producing an oligonucleotide of preselected sequence comprising a plurality of oligonucleotide members comprising one or more oligonucleotide species and having the compositional formula $(X)_a(N)_b$; wherein X represents a non-degenerate nucleotide base and N represents a degenerate nucleotide base; "a" represents the number of non-degenerate nucleotide positions and is from 3 to 8; "b" represents the number of degenerate nucleotide positions and is from 0 to 4 but not greater that "a"; and wherein each of the oligonucleotide species is capable of forming a hybridization complex with at least one other of the oligonucleotide species in the library such that a single ligation event of the hybridization complex with another hybridization complex derived from the library produces a ligation reaction product comprising greater than 12 contiguous nucleotide base pairs.

20 Claims, 6 Drawing Sheets

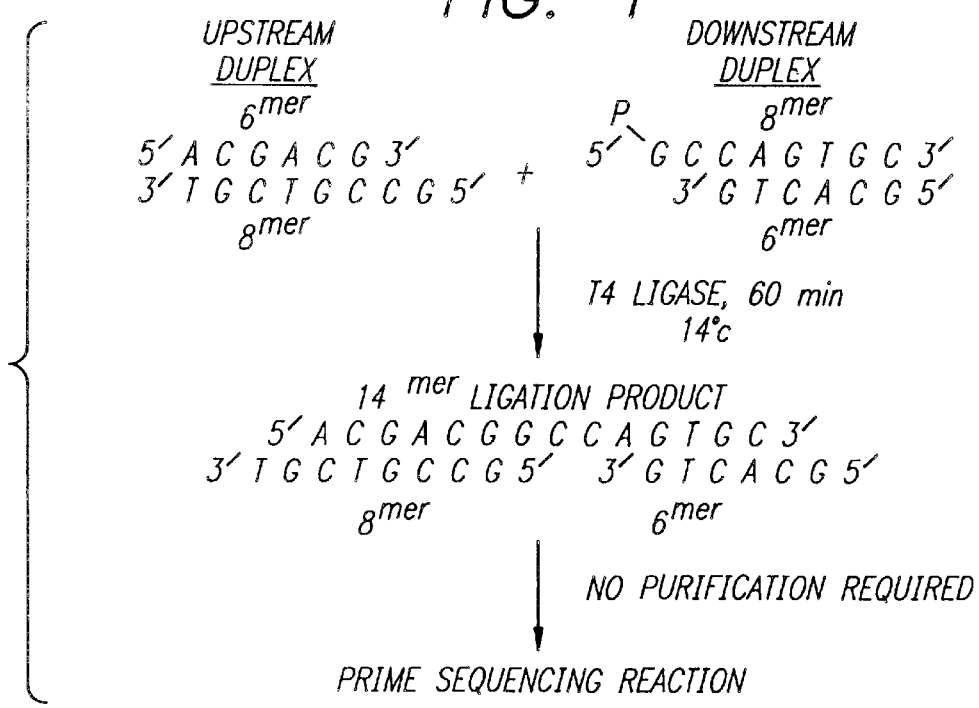
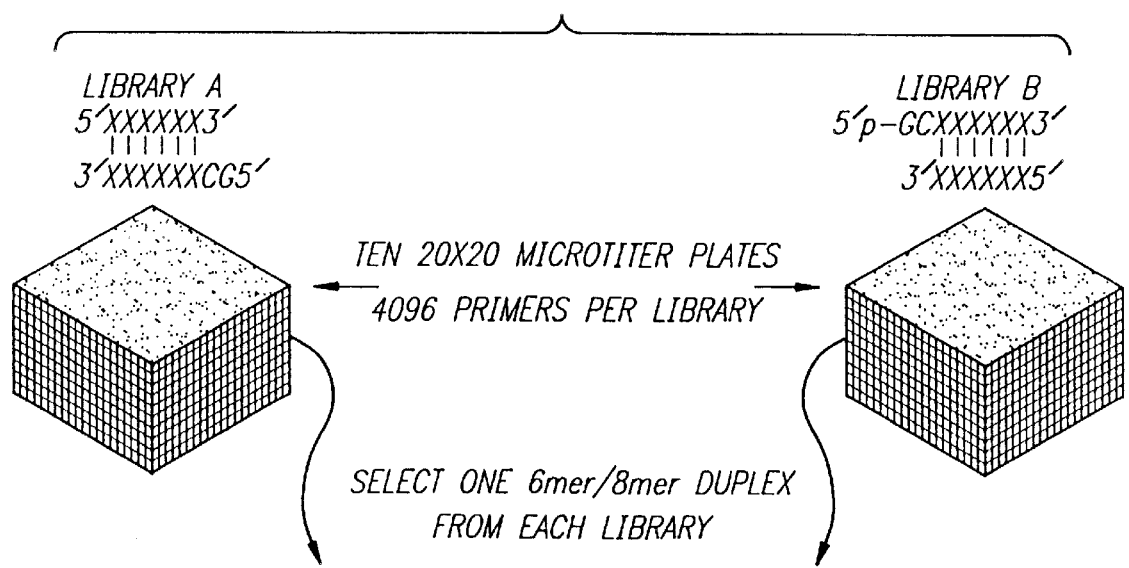
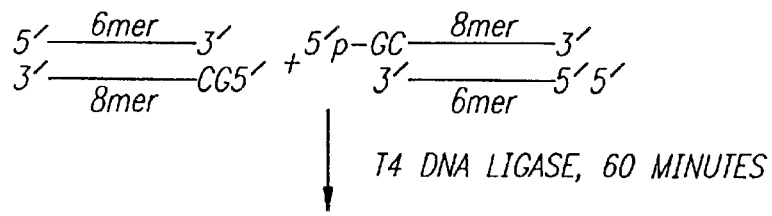
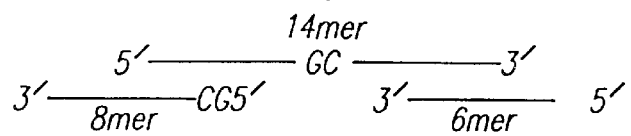
FIG. 1
FIG. 2

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 14 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:1:

A C G A C G G C C A   G T G C                    1 4

( 2 ) INFORMATION FOR SEQ ID NO:2:

( i ) SEQUENCE CHARACTERISTICS:
        ( A ) LENGTH: 16 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:2:

T G A C G A C G T C   C A G T G C                  1 6

( 2 ) INFORMATION FOR SEQ ID NO:3:

( i ) SEQUENCE CHARACTERISTICS:
        ( A ) LENGTH: 19 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:3:

T A A A A C G A C G   A C G G C C A G T              1 9

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: unknown
        (D) TOPOLOGY: unknown (xi) SEQUENCE DESCRIPTION: SEQ ID NO:4:

TGATTCCAAC GAGGAAAGCA CG      22

(2) INFORMATION FOR SEQ ID NO:5:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (xi) SEQUENCE DESCRIPTION: SEQ ID NO:5:

AAACCCGACA GGACTA      16

(2) INFORMATION FOR SEQ ID NO:6:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (xi) SEQUENCE DESCRIPTION: SEQ ID NO:6:

GGTAACTATC GTCTTG      16

(2) INFORMATION FOR SEQ ID NO:7:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (xi) SEQUENCE DESCRIPTION: SEQ ID NO:7:

TTTTCTACGG GGTCTG      16

OLIGONUCLEOTIDE LIBRARIES USEFUL FOR PRODUCING PRIMERS

This application is a national stage filing of International Application PCT/US93/03230, filed Apr. 2, 1993, which is a continuation-in-part of U.S. application Ser. No. 07/863,412, filed Apr. 3, 1992, abandoned. This application is also a continuation-in-part of U.S. application Ser. No. 07/765,694, filed Sep. 25, 1991, abandoned sand a continuation-in-part of U.S. application Ser. No. 07/697,936, filed May 8, 1991, now U.S. Pat. No. 5,599,921.

TECHNICAL FIELD

The present invention relates to libraries of oligonucleotides. In addition, the invention relates to methods using libraries of oligonucleotides to produce longer oligonucleotides of preselected nucleotide sequence.

BACKGROUND

Oligonucleotides are widely utilized in molecular biological manipulations including DNA sequencing, cycle sequencing, polymerase chain reactions, in vitro mutagenesis, cloning methodologies involving polylinkers and adapters, synthesis of genes by hybridization and ligation of multiple oligonucleotides, and the like methods. Traditionally, oligonucleotides are prepared by chemical synthesis methods de novo each time they are required. Chemical synthesis of oligonucleotides is time consuming and costly.

One approach to DNA sequencing is called "primer walking" which utilizes known sequence information of a target nucleic acid to be sequenced to design a distal primer which is then used to obtain additional, downstream sequence information. Although primer walking is conceptually appealing, because of its simplicity and the ordered nature of the sequence information obtained, this method can be is expensive and time-consuming because after each sequence is determined, a new, customized primer must be chemically synthesized. Because a single oligonucleotide synthesis requires the preparation of more oligonucleotide than is required for the single sequencing step to be performed, material is wasted resulting in excess cost, and synthesis time slows the sequential sequencing steps.

Recently, Studier proposed a strategy to simplify the preparation of unique oligonucleotides in the form of a library of pre-synthesized oligonucleotides representing every possible nucleotide sequence in the size range of oligonucleotides from 8 to 10 nucleotides in length. Studier, *Proc.Natl.Acad.Sci.*, 86:6917–6921 (1989). However, the library poses technical difficulties insofar as the library must contain from $4^8$ (65,536) to $4^{10}$ (1,048,576) members, respectively, which is generally considered to be so large as to be unmanageable. In addition, oligonucleotides of 8mer to 10mer length are less preferred sequencing primers than longer oligonucleotides of 12mer to 18mer length.

Szybalski proposed the use of a library of hexameric oligonucleotides comprising every possible combination of nucleotide bases, representing a library having 46 (4,096) members, as a means to reduce the size of the library. Szybalski, *Gene*, 90:177–178 (1990). Theoretically, pairs of hexamers from the library were proposed to be capable of being individually ligated while hybridized to a template to form 12 nucleotide (nt), 18-nt, or 24-nt oligonucleotides in length, thereby forming every possible nucleotide sequence from a library having 4,096 members. This same approach has been described in U.S. Pat. No. 5,114,639 to Blocker.

This approach requires ligation of the hexamer pairs in the presence of template DNA (i.e., DNA molecule to be sequenced).

Accordingly, there continues to exist a need for preparing oligonucleotides suitable for priming PCR, cycle-sequencing and the like reactions without de novo oligonucleotide synthesis or the above-described problems. The present invention meets that need.

BRIEF SUMMARY OF THE INVENTION

It has now been discovered that the problems inherent in the prior art can be overcome by the preparation and use of economically feasible, small libraries of oligonucleotides which allow cohesive-end ligation and construction of longer primers suitable for a variety of uses. Additionally, the methods of the present invention permit the production of an excess of primers in a non-template directed manner.

In accordance with the present invention oligonucleotide compositions and libraries of oligonucleotide compositions are utilized for producing longer oligonucleotides of preselected nucleotide sequence. Difficulties in template-dependent variability of ligation reactions are overcome by avoiding template-dependent ligation, and relying instead upon the use of complementarity in the overhangs of short duplexes of oligonucleotides. It is shown herein that reproducible ligation of oligonucleotides can be obtained between short DNA duplexes having complementary overhangs.

As an example, Scheme I below shows at the first step ligation of two duplexes having complementary dinucleotide overhangs formed by hybridizing two octanucleotides (8mers).

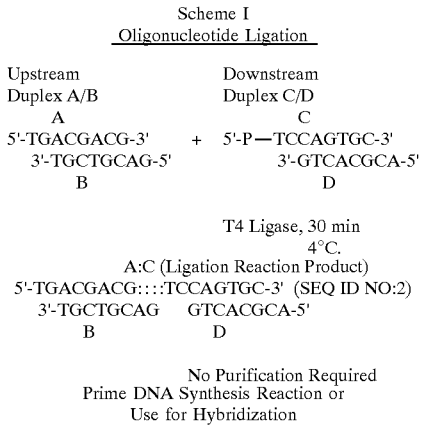

According to Scheme I, 8mer/8mer DNA duplexes are first formed from hybridized 8mer oligonucleotides A, B, C, and D to form a 16mer oligonucleotide primer of preselected sequence designated as an A:C ligation reaction product, representing a ligation of oligonucleotides A and C. The colons (::::) between nucleotide bases indicates the formation of a phosphodiester bond between ligated adjacent bases. The 16mer can be used directly as a primer in a sequencing reaction without purification of the ligation reaction admixture.

As illustrated in Scheme I, the ligation reaction is typically dependent upon the presence of a 5'-terminal phosphate group, where ligation is mediated enzymatically by a ligase, although other ligation chemistries are possible and contemplated. In that regard, the library used in the present method of Scheme I may be provided with or without the 5'-terminal phosphate. If absent, the user of the library may add the phosphate prior to conducting the ligation reaction.

In accordance with a related embodiment of the invention, library size limitations are overcome by the use of degenerate oligonucleotides in which a single oligonucleotide composition contains multiple oligonucleotide species. For example, a representative degenerate octanucleotide composition can be described by the formula 5'-XXNXXNXX-3', where nucleotides (or analogs thereof) designated "X" are the same at any one position for all octanucleotides in the composition (non-degenerate) and nucleotides designated "N" can be any one of A, T, G, C, and preferably a mixture of all four, or analogs thereof (degenerate).

The combination of the specificity of hybridization between complementary duplex overhangs and the non-opposing positions of the degenerate nucleotides in the oligonucleotide compositions allows for a unique solution to problems associated with ligation variability and library size. As an example, Scheme II below illustrates the combination of overhangs and degeneracy in a ligation reaction to favor the formation of a single species of 16mer oligonucleotide reaction product.

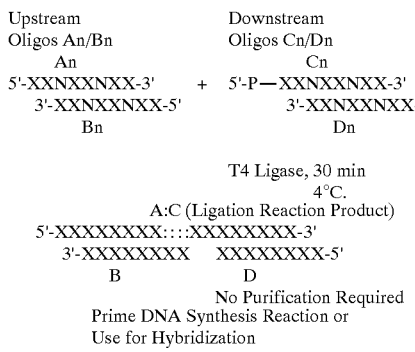

Scheme II
Degenerate Oligonucleotide Ligation

According to Scheme II, 8mer/8mer DNA duplexes are first formed from 8mer oligonucleotides An, Bn, Cn, and Dn, and the resulting overhangs on the duplexes are ligated to form a 16mer oligonucleotide primer of preselected sequence designated as an A:C ligation reaction product. The "n" in the oligonucleotide designation indicates that the oligonucleotide is a degenerate oligonucleotide composition. Furthermore, it is important to note that upon hybridization and ligation of the non-annealing oligonucleotides, the oligonucleotides where N positions destabilize the complex are selected away, and the ligation reaction product is enriched for certain oligonucleotides. The 16mer ligation reaction product can be used as a primer in a sequencing reaction without purification from the ligation reaction mixture.

Following the above approaches, numerous embodiments are contemplated by the present invention, particularly with respect to degenerate oligonucleotides. In one embodiment, the invention contemplates an oligonucleotide library useful for producing an oligonucleotide of preselected sequence comprising a plurality of oligonucleotide members comprising one or more oligonucleotide species and having the compositional formula $(X)_a(N)_b$. "X" represents a non-degenerate nucleotide base and N represents a degenerate nucleotide base. "a" represents the number of non-degenerate nucleotide positions and is from 3 to 8, and "b" represents the number of degenerate nucleotide positions and is from 0 to 4 but not greater that "a". Each of the oligonucleotide species in the library is capable of forming a hybridization complex with at least one other of the oligonucleotide species in the library such that a single ligation event of the hybridization complex with another hybridization complex derived from the library produces a ligation reaction product comprising greater than 12 contiguous nucleotide base pairs.

By "single ligation event" is meant that the formation of a single bond between adjacent nucleotides of a ligation reaction substrate comprised of at least two hybridization complexes forms a double-stranded ligation reaction product having a length greater than 12 contiguous nucleotide pairs.

The combination of two hybridization complexes is typically represented as shown in Scheme II, above. Therefore, in preferred embodiments each hybridization complex comprises at least one unpaired nucleotide. Preferably, the complex has one to three unpaired (overhanging) nucleotides, and more preferably has two unpaired nucleotides.

A particularly preferred oligonucleotide library has the compositional formula is selected from the group consisting of $(X)_5(N)_1$, $(X)_4(N)_2$, $(X)_6(N)_1$, $(X)_5(N)_2$ and $(X)_6(N)_2$, particularly $(X)_6(N)_2$, and more particularly 5'-XXNXXNXX-3'.

Also contemplated by the invention is a kit useful for producing an oligonucleotide primer of preselected sequence comprising, in separate enclosures, one or more libraries of the invention. A kit may also include a suitable ligase and/or a polymerase for use in practicing the methods of the invention.

Further in accordance with the present invention are methods for producing an oligonucleotide of preselected nucleotide sequence using one or more oligonucleotide members from a library of the invention. A preferred method comprises the steps of:

a) selecting at least one oligonucleotide member from a library according to the invention;
b) hybridizing in an aqueous ligation buffer the oligonucleotide member(s) selected in step (a) having a preselected nucleotide sequence and capable of hybridizing to form a ligation reaction substrate; and
c) ligating the ligation reaction substrate to form a ligation reaction product containing the oligonucleotide of preselected nucleotide sequence.

Also in accordance with the present invention, oligonucleotide compositions useful for producing oligonucleotide primers or hybridization probes are provided. In one embodiment, the oligonucleotide compositions comprise a plurality of different oligonucleotide species each having the compositional formula $(X)_a(N)_b$ and a length of from 5 to 12 nucleotides; wherein X represents a non-degenerate nucleotide base and N represents a degenerate nucleotide base; "a" represents the number of non-degenerate nucleotide positions and is from 3 to 8; "b" represents the number of degenerate nucleotide positions and is from 0 to 4 but not greater that "a". In preferred embodiments the nucleotides X and N are the nucleotide bases A, T, G, C, or analogs thereof.

Particularly preferred is an oligonucleotide composition wherein the oligonucleotide species in the composition each have a nucleotide sequence according to the compositional formula selected from the group consisting of $(X)_5(N)_1$, $(X)_4(N)_2$, $(X)_6(N)_1$, $(X)_5(N)_2$ and $(X)_6(N)_2$ particularly $(X)_6(N)_2$, and more particularly 5'-XXNXXNXX-3'.

Other embodiments will be apparent to one skilled in the art.

BRIEF DESCRIPTION OF THE DRAWINGS

FIG. 1 illustrates a typical ligation reaction scheme according to one embodiment using 6mer/8mer DNA duplexes as examples to form a 14mer oligonucleotide primer of preselected sequence.

FIG. 2 is a flow chart diagramming the steps in a ligation method for producing an oligonucleotide having a preselected nucleotide sequence using two libraries (A and B) according to the methods described herein. The flow chart shows a preferred embodiment using 6mer/8mer duplex DNA molecules having cohesive GC termini, with the 8mer oligonucleotide of library B having a phosphorylated 5' terminus to form a 14mer.

DETAILED DESCRIPTION OF THE INVENTION

Definitions

Figure 3:
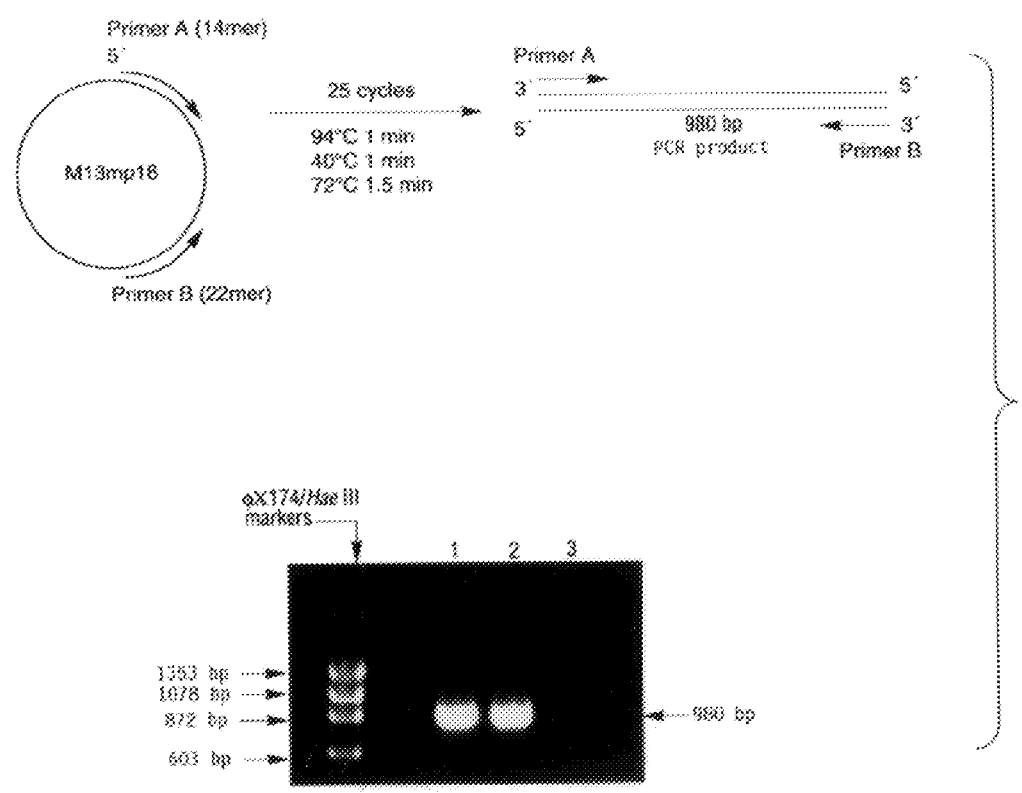
FIG. 3 illustrates an agarose gel electrophoretic analysis of the polymerase chain reaction (PCR) product formed using an oligonucleotide primer (14mer) produced according to the ligation reaction shown in FIG. 1 as described in Example 3. The schematic in the upper portion of FIG. 3 illustrates the amplification by PCR of a 980 base pair (bp) fragment from an M13mp18 using a primer pair (primers A and B). The lower portion of FIG. 3 illustrates the agarose gel analysis showing that the 980 bp PCR product was amplified from ssM13mp18 using the following primer pairs: Lane 1, 19mer primer A' and 22mer primer B (both chemically synthesized); Lane 2, 14mer primer A (created by ligation) and 22mer primer B (chemically synthesized); Lane 3, 6mer/8mer (no ligase control) and 22mer primer B. Also shown is a lane of PhiX174/Hae III markers containing 1353, 1078, 872 and 603 bp fragments. The primer sequences are shown in Table 1 at page 62.

Nucleotide: as used herein refers to a monomeric unit of DNA or RNA consisting of a sugar moiety (pentose), a phosphate, and a nitrogenous heterocyclic base, or a functional analog thereof. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. The nucleotides are adenine, thymine, cytosine, guanine, uracil, and analogs thereof.

Base Pair (bp): A partnership of the nucleotides adenine (A) with thymine (T), or of cytosine (C) with guanine (G) in a double stranded DNA molecule. In RNA, uracil (U) is substituted for thymine. Nucleotide analogs may also pair up to form a base pair so long as the partnership is specific and complementary in a manner analogous to the above nucleotides.

Nucleic Acid: A polymer of nucleotides, either single or double stranded.

Oligonucleotide: The term "oligonucleotide" or "oligo" as used herein in reference to primers, probes and nucleic acid fragments or segments is defined as a polymeric molecule comprised of a plurality of deoxyribonucleotides, ribonucleotides, or analogs thereof, preferably at least 5. Its exact size will depend on many factors, which in turn depends on the ultimate conditions of use.

Gene: A nucleic acid whose nucleotide sequence codes for an RNA or polypeptide. A gene can be either RNA or DNA.

Complementary Bases: Nucleotides or analogs thereof that normally pair up when oligonucleotides adopt a double stranded configuration. Chemical modifications to the ribose or phosphate backbones, or to the bases, can be incorporated to form a nucleotide analog so long as the analog does not inhibit hybridization with another oligonucleotide, or analog thereof, and the analog has its own specific complementary base.

Complementary Nucleotide Sequence: A sequence of nucleotides in an oligonucleotide capable of hybridizing to another oligonucleotide for a length of time sufficient to permit a desired event, e.g., a ligation reaction, a primer extension reaction, or ligand detection.

Conserved: A nucleotide sequence is conserved with respect to a preselected (reference) sequence if it non-randomly hybridizes to an exact complement of the preselected sequence.

Library: A collection of separate oligonucleotide compositions, each composition representing a different member of the library, and each present in a separate enclosure.

Hybridization: The pairing of substantially complementary nucleotide sequences to form a duplex or heteroduplex by the establishment of hydrogen bonds between complementary bases. It is a specific, i.e. non-random, interaction between two complementary polynucleotides that can be competitively inhibited.

Nucleotide Analog: A purine-like or pyrimidine-like nucleotide that differs structurally from A, T, G, C, or U, but is sufficiently similar in function to substitute for the normal nucleotide in an oligonucleotide nucleic acid molecule and participate in complementary hybridization with a complementary nucleotide.

Overhang: A region of single strandedness at a termini of a double-stranded (duplex) oligonucleotide molecule that is typically available to hybridize to a complementary single-stranded overhang.

Upstream: In the direction opposite to the direction of DNA transcription, and therefore going from 5' to 3' on the non-coding strand, or 3' to 5' on the coding strand or mRNA.

Downstream: Further along a DNA sequence in the direction of sequence transcription, that is traveling in a 3'- to 5'-direction along the non-coding strand of the DNA or a 5'- to 3'-direction along the coding strand.

B. Oligonucleotide Libraries

The present invention provides a means for the rapid and inexpensive synthesis of oligonucleotides of preselected sequence for use in DNA sequencing, cycle sequencing, polymerase chain reaction (PCR) procedures, and other applications requiring oligonucleotides. The approach described herein utilizes oligonucleotide compositions that are used to form longer oligonucleotides of preselected sequence suitable for use as primers in molecular biological manipulations, particularly DNA sequencing and PCR, or as hybridization reagents.

Typically, an oligonucleotide composition of this invention is organized with other oligonucleotide compositions into a collection, or library, comprised of a plurality of different library members, each member representing a different oligonucleotide composition containing oligonucleotide species of known sequence. Users of the library select those members which, upon ligation according to the methods described herein, form a longer oligonucleotide of preselected sequence suitable for use as a primer or hybridization reagent.

A library of this invention is comprised of different members (oligonucleotides or oligonucleotide compositions) each present in a separate enclosure and each having different nucleotide sequence(s). The oligonucleotides in an individual enclosure can be homogeneous, i.e., all oligonucleotide molecules in an enclosure are identical in sequence. Alternatively, the oligonucleotides in an individual enclosure can be heterogeneous, i.e., the enclosure contains an oligonucleotide composition of this invention having oligonucleotides of different but related nucleotide sequences (i.e., degenerate).

Thus a library of this invention comprises a collection (plurality) of oligonucleotide members, each having a different preselected nucleotide sequence, that can be used to construct larger oligonucleotides of preselected sequence by combining the members. In order to construct any possible nucleotide sequence by combining members, the library preferably contains every possible combination of nucleotide sequence.

The size of the library that has no degeneracies is determined by the expression $4^n$ where the superscript "n" represents the number of bases in each of the oligonucleotide subunits making up the library. Thus, a small increase in oligonucleotide length dramatically increases the size of the library. For example, a library of oligos having 6 nucleotide bases, also referred to as a 6mer, contains 4096 different oligos, whereas a 9mer library has over 260,000 primers.

The library, in one embodiment typically has at least 100 members, preferably about 100 to 100,000 different members, and more preferably 1,000 to 60,000 members. Consistent with the objectives herein for reducing a library size, a library of less that 30,000 members is particularly preferred, and even more preferably contains about 1,000 to 5,000 members.

Each member of a library of this invention comprises one or more oligonucleotide species and typically has a length of at least 5 nucleotides, preferably 5 to 12 nucleotides, more preferably about 5 to 10 nucleotides, and particularly about 6 to 8 nucleotides, although longer oligonucleotides can be present in the library.

In a preferred embodiment a library contains a plurality of different oligonucleotide members which are degenerate oligonucleotide compositions according to the present invention. Although other oligonucleotide libraries are described herein, those containing degenerate oligonucleotide compositions are particularly preferred because the degeneracy reduces the size of the library without limiting capacity or usefulness of the library, thereby reducing manufacturing costs and library management.

The use of degenerate oligonucleotide compositions in the present invention is particularly advantageous in that it significantly reduces the library size needed to provide every possible nucleotide sequence in the oligonucleotides of the library. Of course, the degree of library size reduction is a function of the number of degenerate nucleotide positions included in a oligonucleotide.

Thus, in one embodiment, the invention provides an oligonucleotide library useful for producing an oligonucleotide of preselected sequence comprising a plurality of oligonucleotide members comprising one or more oligonucleotide species and having the compositional formula $(X)_a(N)_b$, wherein X represents a non-degenerate nucleotide base and N represents a degenerate nucleotide base, "a" represents the number of non-degenerate nucleotide positions and is from 3 to 8, and "b" represents the number of degenerate nucleotide positions and is from 0 to 4 but not greater that "a". Each oligonucleotide species of the library in this embodiment is capable of forming a hybridization complex with at least one other oligonucleotide species in the library such that a single ligation event of the hybridization complex with another hybridization complex derived from the library produces a ligation reaction product comprising greater than 12 contiguous nucleotide base pairs.

As described for the degenerate oligonucleotide compositions of this invention, the library can comprise any combination of lengths, number of degenerate nucleotides, and choices of nucleotide bases within the degenerate nucleotide position. Preferred degenerate libraries comprise oligonucleotide members according to a compositional formula selected from the group consisting of $(X)_5(N)_1$, $(X)_4(N)_2$, $(X)_6(N)_1$, $(X)_5(N)_2$ and $(X)_6(N)_2$, such that the position of the degenerate nucleotide(s) can be at any of a variety of positions. A particularly preferred degenerate library comprises octanucleotide members according to the compositional formula $(X)_6(N)_2$. Exemplary of this preferred embodiment is a library with a degenerate octanucleotide composition having two degenerate positions, thereby requiring 4,096 different compositions in order to account for all possible sequences. A particularly preferred library contains 4,096 different octanucleotide compositions, wherein each composition comprises octanucleotides according to the formula: 5'-XXNXXNXX-3' as described herein.

In an alternate embodiment, each oligonucleotide member in a library comprises one or more species of oligonucleotide having a sequence that is complementary with at least one other species of the library along a linear (contiguous) stretch of nucleotides. Thus, each species of this library has a nucleotide sequence such that it can form, upon complementary hybridization with another species of the library, a double-stranded (ds) duplex DNA molecule having an overhang on at least one terminus. The individual species of this library can vary in length and in sequence from one another, so long as the library is designed as defined herein to allow the selection of hybridizable pairs to form duplex DNA having the overhangs as required to practice the methods of this invention.

In another embodiment, a library is comprised of a plurality of enclosures, each enclosure containing a different oligonucleotide species having a "common" (i.e., shared by all the oligonucleotide species in the library) nucleotide sequence of at least 1 nucleotide, and preferably from 1 to 3 nucleotides, in length located at one terminus of the oligonucleotide, which terminus is the same in each oligonucleotide species of the library.

The oligonucleotide species in a library in this embodiment can therefore be represented by the formula YZ, where Y represents the nucleotide sequence that is the same (common) in all species of the library, and Z represents the nucleotide sequence that is different for each species of the library. Preferably, Z defines the region of complementarity when present in a duplex of the present invention such that the overhang in the duplex is defined by the sequence represented by Y. Y is at least one nucleotide in length, preferably from 1 to 3 nucleotides in length, more preferably 2 nucleotides long, and Z can be from 5 to 10 nucleotides in length, preferably 6 to 8.

A library preferably contains all possible nucleotide sequences definable with a four nucleotide base (A, T, G, and C) vocabulary in a given length. Thus, a library where X or Z is six nucleotides in length preferably has 4,096 different members.

However, there are instances where less than all four bases are desired at a certain nucleotide position in members of the library. For example, a certain position in the oligonucleotide may be limited to only GC (such at a two base terminal portion).

In one embodiment, Y defines the 5' terminus of the oligonucleotide. In another embodiment, all the members of the library have a 5' phosphate, preferably at the 5' terminus of the oligonucleotide. In another embodiment, the invention contemplates a library where all the oligonucleotide members are free from phosphate.

Particularly preferred oligonucleotide libraries are comprised of oligonucleotides as described above but having a dinucleotide termini that has a sequence selected from the group consisting of GG, CC, TT, AA, TC, CT, GA, AG, TG, GT, AC, CA, NI and IN, where N is selected from the group consisting of A, T, G and C, and where I is inosine. Alternatively, the dinucleotide termini can be CI, IC, TA or AT for the reasons described herein.

Degenerate Oligonucleotide Compositions

In a related embodiment, the present invention provides oligonucleotide compositions each comprising a population of sequence-related oligonucleotide species which differ in nucleotide sequence only at preselected nucleotide positions. The nucleotide base difference in these compositions can be represented as the letter "N", designating A, T, G, or C (or analogs thereof) at that position as in, for example, an 8mer oligonucleotide composition having the formula 5'-XXNXXNXX-3', wherein X designates the nucleotide bases in the sequence of the oligonucleotide that are common to all oligonucleotide species within the composition. The N position may, but need not necessarily, comprise all possible nucleotide bases, or analogs thereof.

Oligonucleotide compositions in which at least one nucleotide base position is represented by an "N" are referred to as degenerate oligonucleotide compositions because the oligonucleotide species in the composition, although different in part, contain redundancies with regard to their respective sequences at positions of the sequence defined by an X that is the same in each oligonucleotide species in the composition.

In one embodiment, the invention contemplates degenerate oligonucleotide compositions in which nucleotides at the position "N" is within the region of the oligonucleotide species of the composition selected to hybridize to a complementary oligonucleotide species (partner) in the duplex. An example of this embodiment is represented by the formula for a 6mer/8mer duplex:

5'-XXXXXX-3'

3'-XXNXXNXX-5'

In the above example the degenerate nucleotides (N) are at positions 3 and 6 of the 8mer when positions are counted in the direction of 5' to 3', and can be referred to as $N_3$ and $N_6$. Such an 8mer is referred to as an $N_3,N_6$-8mer oligonucleotide composition. It is to be appreciated that other formulas can also be suitably utilized to designate oligonucleotide compositions in this embodiment, by placing a degenerate nucleotide at any position in the oligonucleotide such as is shown by any of the following representative 8mer compositions: $N_1,N_2$-; $N_1,N_3$-; $N_1,N_4$-; $N_1,N_5$-; $N_1,N_6$-; $N_1,N_7$-; $N_1,N_8$-; $N_2,N_3$-; $N_2,N_4$-; $N_2,N_5$-; $N_2,N_6$-; $N_2,N_7$-; $N_2,N_8$-; $N_3,N_4$-; $N_3,N_5$-; $N_3,N_6$-; $N_3$, $N_7$-; $N_3,N_8$-; $N_4,N_5$-; $N_4,N_6$-; $N_4,N_7$-; $N_4,N_8$-; $N_5,N_6$-; $N_5,N_6$-; $N_5,N_8$-; $N_6,N_7$-; $N_6,N_5$- and $N_7,N_8$-. Thus, octanucleotide embodiments where there are two degenerate (N) nucleotides and six conserved nucleotides (X) can be represented generally by the compositional formula $(X)_6(N)_2$. Extending this formula, the present invention also provides an oligonucleotide composition according to the compositional formula $(X)_a(N)_b$ wherein "a" can be from 3–8 and "b" can be from 0–4 but is not greater than "a".

As used herein, the term "compositional" indicates the molar ratio of the elements (nucleotides) in the formula irrespective of the order or placement of the "N" residues relative to the "X" residues.

Degenerate 8mer compositions can be admixed with other complementary nucleotides to form an admixture comprising a duplex having at least one overhang, such as an $N_3,N_6$-8mer/$N_3,N_6$-8mer duplex or a 6mer/$N_3,N_6$-8mer duplex.

Although there are 16 different $N_3,N_6$-8mer species in a composition, only one of the 16 species is the most energetically favorable complement to the admixed complementary oligonucleotides and thus favored to form a duplex. Upon use in a ligation reaction of this invention, the duplexed $N_3,N_6$-8mer will preferentially participate in the ligation reaction to form the preselected ligation reaction product as can be represented by the equation:

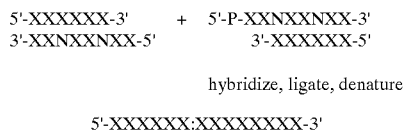

The above ligation reaction product is represented as 5'-XXXXXX:XXXXXXXX-3' without any N's because the selectivity of complementary hybridization can will produce a predominant species of ligation reaction product complementary to the template. Stated differently, the hybridization conditions can be selected to be sufficiently stringent to greatly favor the desired complementary oligonucleotides to be selected and ligated from the degenerate pool of oligonucleotides. Therefore, reaction schemes are shown with a loss of the "N" upon formation of the ligation reaction product to indicate the selectivity of the hybridization reaction upon ligation with a complementary sequence.

The above hybridization and ligation reactions can be utilized with the degenerate nucleotides at any of the positions hybridizing in the duplex, and need not be limited to positions $N_3$ or $N_6$. In addition, the degenerate nucleotide positions can be different in the two duplexes (A & B) to be ligated. Furthermore, as will be readily apparent to one skilled in the art, this embodiment can be practiced using multiple degenerate nucleotides and need not be limited to the use of two degenerate positions in an 8mer. Additionally, the degenerate nucleotides (N) can be in any of the oligonucleotides to be ligated, either or both upper (or lower) oligonucleotides, either or both upstream (or downstream) oligonucleotides, in all four oligonucleotides, or any combination thereof.

Desirable and preferred conditions for obtaining reproducible results in the practicing the present embodiment using degenerate oligonucleotide compositions are (1) to use molar excesses of the degenerate oligonucleotides relative to non-degenerate oligonucleotides to favor formation of the desired duplex, such as a 16 fold molar excess of $N_3,N_6$-8mer relative to 6mer, and (2) to use hybridization conditions that favor formation of complementarity in the duplexes, so as to reduce the production of unwanted ligation reaction products. Hybridization conditions can be controlled by presently known variables to favor complementary hybridization. Where both oligonucleotides are degenerate, the molar ratio is preferably adjusted so that the target species are equimolar.

In a particularly preferred embodiment, the invention relies on several of the above elements. A preferred composition of degenerate 8mer oligonucleotides (octanucleotides) is defined by the compositional formula 5'-XXNXXNXX-3'. All of the nucleotides in the composition have the same sequence at positions designated by "X", thereby defining a common sequence between all species of oligonucleotide within the composition. Furthermore, the composition contains different oligonucleotides whose sequences differ by the presence of the degenerate position nucleotide "N". Preferably, all four possible nucleotide bases, or their respective analogs, are represented in all possible combinations such that a composition contains oligonucleotide species representing every possible sequence defined by the formula. Thus, where there are two degenerate positions "N", there can be 16 different is oligonucleotide species.

In a preferred embodiment, the composition of octanucleotides each have a 5' terminal phosphate to facilitate ligation.

A particularly preferred ligation scheme utilizing degenerate 8mer/8mer duplexes where one of the 8mers has a 5' terminal phosphate is shown in reaction Scheme II. Following reactions as shown in Scheme II, a requirement for production of a single preselected ligation reaction product when using a degenerate oligonucleotide composition is that the non-ligated overhangs (5' termini of An or Dn) should not hybridize efficiently (1) to each other, (2) to the ligated center overhangs (5' termini of Bn or Cn), or (3) to themselves.

Using the ligation reaction of Scheme II, one can produce any 16mer of a preselected nucleotide sequence using only a library of 4,096 different $(X)_6(N)_2$ octanucleotide compositions.

The ligation reaction of Scheme II was used in Example 5 with degenerate 8mer oligonucleotide compositions, and the resulting ligation reaction product was used in cycle sequencing (Example 6), in reverse transcriptase sequencing (Example 7), and in sequencing reactions using a modified $T_7$ DNA polymerase (Example 8).

In one embodiment, the invention contemplates compositions and methods that utilize a degenerate 8mer oligonucleotide composition according to the formula 5'-NNXXXXXX-3'. Each composition has 16 different oligonucleotide species in which the sequence NN can be AA, AT, AG, AC, TT, TA, TG, TC, GG, GA, GT, GC, CC, CA, CT, CG, or analogs thereof which allow specific and complementary hybridization.

When a degenerate 8mer composition is used according to the present invention in a 6mer/8mer duplex, for example, the sequence NN can be positioned in the 2-base overhang in which case the resulting ligation product is represented by the formula:

In this embodiment, 16 different 14mer ligation reaction products are formed rather than a single 14mer oligonucleotide. When used as a primer, however, the species with favorable energy complementarity will hybridize and prime the target, and the non-favorable species do not participate in hybridization to template. A colon (:) between oligonucleotides is used to indicate that the adjacent nucleotides have become ligated. Thus, the ligation of degenerate oligonucleotides in this embodiment can be represented as follows:

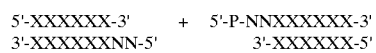

hybridize, ligate, denature

In a related embodiment, the invention describes the use of degenerate oligonucleotides of various lengths to form ligation reaction products from multiple oligonucleotides. By selection of "nested" overlapping oligonucleotides that serve as templates for one another, one can build 18mers, 22mers, 24mers, 30mers, and the like. In this embodiment, one or more degenerate oligonucleotide compositions provide regions of complementarity for hybridization of two unique oligonucleotides, having at least four nucleotides of complementarity to each of the two oligonucleotides to be ligated. The template overlaps and thereby joins both unique oligonucleotides.

In accordance with this embodiment, two different degenerate 8mer compositions can be used to direct the ligation of three oligonucleotides, A, B, and C as follows:

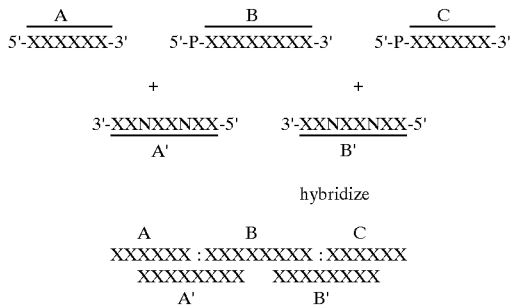

One skilled in the art having the benefit of the present disclosure will appreciate that additional permutations for using the degenerate oligonucleotide compositions are provided by the present invention. For example a 22mer can be produced by combining a 6mer/8n-mer (i.e., a degenerate 8mer) duplex, an 8n-mer/8n-mer duplex, and an 8n-mer/6mer duplex as follows:

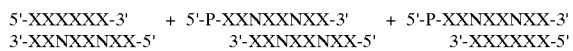

Similarly, a 24mer oligonucleotide can be produced using a 6mer/8n-mer duplex, a 6mer-6mer/8n- mer triplex, and a 6mer/8n-mer duplex, as follows:

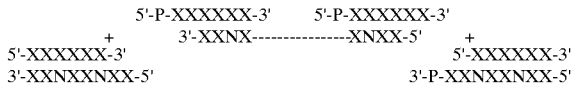

or using three 8n-mer/8n-mer duplexes as follows:

Other possible combinations are readily apparent, and therefore the invention need not be limited by the above examples.

Double-Stranded (Duplex) DNA Libraries

One contemplated class of libraries of the invention contains double-stranded (duplex) DNA molecules, referred to as duplex DNA or a duplex. For example, using a 6mer/8mer duplex as exemplary, a library would have up to 4096 different members representing all possible nucleotides sequences in the hexanucleotide (6mer) component of the 6mer/8mer duplex. All members of the library have the same nucleotide sequence in the overhang. Typically, each different duplex is present in a separate enclosure.

In accordance with the present invention, two or more double-stranded (ds) DNA duplexes which have complementary overhanging (cohesive) termini are ligated to form a ligation reaction product comprising a larger oligonucleotide of preselected sequence. The cohesive termini on the duplexes increase the specificity and reaction rate of the ligation reaction. The use of a DNA duplex comprised of two complementary 8mers (an 8mer/8mer duplex) having a two nucleotide overhang is used as exemplary, and is shown in Scheme I. The downstream duplex preferably contains a phosphate group on the 5' terminus of 8mer oligonucleotide "C" to provide a ligation substrate for DNA ligase. Note that the ligation reaction produces a 16mer ligation reaction product on the upper (sense) strand and two non-ligated oligonucleotides on the lower (non-coding) strand because of the absence of a 5'phosphate on the 5' end of the 8mer designated "B".

All duplexes of the invention have two domains: at least one overhang, and a region of complementarity between the oligonucleotides of the duplex. Two overhangs arise, for example, where two 8mer oligonucleotides are offset in complementarity to form a duplex having a region of 6 hybridized nucleotides and having two nucleotides in an overhang at each termini.

In one preferred embodiment, the oligonucleotide of the duplex providing the overhang is adapted for ligation to the terminal 3' nucleotide of another oligonucleotide to direct ligation between two duplexes, designated upstream and downstream duplexes to connote that upon ligation, a single, ligated oligonucleotide of preselected sequence is formed. Such adaptation is preferably in the form of a 5'-terminal phosphate on one overhanging oligonucleotide and a 5'-terminal hydroxyl group on the other overhanging oligonucleotide to permit enzymatic ligation of only one strand and not its complementary oligonucleotide. Other reactive moieties that function as the adaptation means may also be applied to the present technology as to provide directed ligation, and are therefore contemplated.

Thus the library can be provided with or without a 5' phosphate on the oligonucleotide of the duplex that contributes to the overhang. For example, in one embodiment of a 6mer/8mer duplex library, the 5' terminus of all the 8mers in the library contain a phosphate. Alternatively, a single library can be provided that lacks a 5' terminal phosphate, and the user can add the 5' terminal phosphate as needed.

Phosphorylation of the 5' termini of oligonucleotides is well known in the art. A useful phosphorylating reaction admixture comprises 30 microliters (ul) of a reaction buffer containing 50 Mm Tris-Hcl, Ph 7.5, 10 Mm $MgCl_2$, 5 Mm DTT, 0.1 to 10 micrograms (ug) of oligonucleotide, 1 Mm ATP, 50 micrograms of bovine serum albumin and 20 units of bacteriophage T4 polynucleotide kinase. The phosphorylating admixture is then maintained (incubated) at 37° C. for 30 minutes, whereupon the reaction is stopped, typically by adding 1 $\mu$l of 0.5M EDTA to the maintained admixture. If desired, [gamma-$^{32}$P] ATP can be added to the reaction to produce labeled oligonucleotide.

In one embodiment, the invention contemplates matched first and second libraries, where the first library comprises 6mer/8mer duplexes lacking a 5'phosphate on the 8mer, and the second library comprises 6mer/8mer duplexes each having a 5'phosphate. The libraries are "matched" because the overhangs of the oligonucleotides in the first library are complementary to the overhangs in the second library.

An example of two matched libraries is shown in FIG. 2, wherein the first and second libraries (represented as libraries A and B) each comprise up to 4096 different duplex DNA members present in separate wells of a microtiter plate, each member comprised of a 6mer/8mer duplex and having complementary GC overhangs formed by the 8mer component.

Thus one embodiment contemplates a library comprised of a plurality of members, each member comprising a different duplex. Each duplex member of the library is present in a separate enclosure (package). Each duplex member has a unique nucleotide sequence and each duplex in the library has the same nucleotide sequence in the overhang region of the duplex. The region of complementarity in the duplexes of the library is at least 5, and preferably from 5 to 7, nucleotides in length, thereby defining the size of the library. Preferably the region of complementarity, and therefore the length of the shorter oligonucleotide of the duplex is 6 nucleotides, and therefore the library has a size of 4096 oligonucleotide members. The overhang is at least one nucleotide, and preferably is 1 to 3 nucleotides in length.

A preferred library has a dinucleotide overhang where the overhangs have a sequence selected from the group consisting of GG, CC, TT, AA, TC, CT, GA, AG, TG, GT, AC, CA, NI and IN, where N is selected from the group consisting of A, T, G and C, and where I is inosine.

Because the primers produced by the present invention are to be utilized in primer extension reactions, the presence of a common region of sequence in the center of the primer derived from the overhang puts a limitation on the use of the primer. To find a complementary match in a template, one must scan a region of the template for the occurrence of the common sequence in order to design a primer to that region. For example, if the library used has a two base overhang, e.g., TC, then template must be scanned for the presence of the complementary AG in order to design a primer to hybridize to that region. The statistical likelihood of locating a AG in a random sequence is one in 16.

It is preferred to design the overhang in a manner to reduce the amount of template sequence that must be scanned in order to locate a match to the overhang region of the primer being produced by the present methods.

To that end, libraries having the overhanging nucleotide sequence NI or IN are preferred, particularly CI or IC. By this design, both the first and second libraries can have the same termini, thereby reducing the number of different libraries required to represent every possible sequence. The presence of inosine (I) in the resulting oligonucleotide primer increases the probability of identifying a template sequence having a sequence complementary to the region of the primer derived from the overhang region, as discussed herein.

In another embodiment, the invention contemplates the use of the dinucleotide TA or AT in the overhang region. Because thymidine is a small pyrimidine, a mismatch in the overhang region when the oligonucleotide is used as a primer can be tolerated. The internally mismatched nucleotide "T" in the primer will still allow the primer to effectively prime PCR and sequencing reactions. Thus, this approach also increases the probability of finding a sequence in a template to be primed that has complementarity to the primer oligonucleotide.

Oligonucleotide Synthesis

The oligonucleotide compositions of the present invention can be prepared using any suitable method, such as, for example, the phosphotriester or phosphodiester methods known in the art; see Narang et al., *Meth. Enzymol.*, 68:90, (1979); U.S. Pat. No. 4,356,270; and Brown et al., *Meth. Enzymol.*, 68:109, (1979). Exemplary synthesis is described in Example 1.

The oligonucleotides can be labeled, i.e., operatively linked to an indicating means or group, and used to detect the presence of a specific nucleotide sequence in a target template. Typically such indicating means is a label such as radioactive atoms, chemically modified nucleotide bases, and the like.

Radioactive elements operatively linked to or present as part of a oligonucleotide provide a useful means to facilitate the detection of a DNA duplex. A typical radioactive element is one that produces beta ray emissions. Elements that emit beta rays, such as $^3H$, $^{12}C$, $^{32}P$, $^{33}P$ and $^{35}S$ represent a class of beta ray emission-producing radioactive element labels. A radioactive oligonucleotide is typically prepared by enzymatic incorporation of radioactively labeled nucleotides into a nucleic acid using DNA kinase.

Alternatives to radioactively labeled oligonucleotides are oligonucleotides that are chemically modified to contain metal complexing agents, biotin-containing groups, fluorescent compounds, and the like.

One useful metal complexing agent is a lanthanide chelate formed by a lanthanide and an aromatic beta-diketone, the lanthanide being bound to the nucleic acid or oligonucleotide via a chelate forming compound such as an EDTA-analogue so that a fluorescent lanthanide complex is formed. See U.S. Pat. No. 4,374,120, Pat. No. 4,569,790 and published Patent Application Nos. EP0139675 and WO87/02708.

Biotin or acridine ester-labeled oligonucleotides and their use to label oligonucleotides have been described. See U.S. Pat. No. 4,707,404, published Patent Application EP0212951 and European Patent No. 0087636. Useful fluorescent marker compounds include fluorescein, rhodamine, Texas Red, NBD and the like.

A labeled oligonucleotide present in a DNA duplex renders the duplex itself labeled and therefore distinguishable over other nucleic acids present in a sample to be assayed. Detecting the presence of the label in the duplex and thereby the presence of the duplex, typically involves separating the DNA duplex from any labeled oligonucleotide probe that is not hybridized to a DNA duplex.

Techniques for the separation of single stranded oligo, such as non-hybridized labeled oligo, from DNA duplex are well known, and typically involve the separation of single stranded from double stranded nucleic acids on the basis of their chemical properties. More often separation techniques involve the use of a heterogeneous hybridization format in which the non-hybridized probe is separated, typically by washing, from the DNA duplex that is bound to an insoluble matrix. Exemplary is the Southern blot technique, in which the matrix is a nitrocellulose sheet and the label is $^{33}P$ or $^{32}P$. Southern, *J. Mol. Biol.*, 98:503 (1975).

Nucleotide bases other than the common four nucleotides (A,T,G or C), or the RNA equivalent nucleotide uracil (U), can be used in the present invention and are designated nucleotide analogs. Thus, for convenience, the term "nucleotide base" is meant, in the context of the present invention to include all possible compounds that can function in the present invention, including common deoxy- or ribonucleotides, nucleotide analogs, and other chemical compounds which might be developed that are suitable for use in a "oligonucleotide" having the property of being incorporated in a duplex DNA molecule without destabilizing the structure of the duplex, and facilitating complementary hybridization. Thus a nucleotide base can be an analog that is a nucleoside with a non-destabilizing moiety, such as a non-protruding side group, phosphate backbone analogs, ribose or deoxyribose analogs, and the like analogs.

By non-destabilizing hybridization is meant that the nucleotide can participate in DNA-DNA or DNA-RNA (or analog) duplex formation (base pairing) without significantly preventing the ordinary complementary hybridization of adjacent nucleotides in the oligonucleotide that would otherwise hybridize to their complement. Inosine is an example of a non-destabilizing hybridizable nucleotide, with specificity for A, T or C, but not G. Other nucleotides having this property can also be used in the present invention.

In addition, other modifications are contemplated that are designed to increase an oligonucleotide's resistance to degradation by exonucleolytic enzymes. A preferred modification is to have a thio-phosphodiester linkage between the terminal and penultimate nucleotide at the 3' terminus of an oligonucleotide used in a library or method of this invention.

Synthesis of degenerate oligonucleotide compositions is accomplished nearly the same as homogeneous oligonucleotide compositions, and can be accomplished by a variety of synthetic chemical means that are not to be construed as limiting to the present invention. Typically, where the synthesis step is to be carried out adding the nucleotides A, T, G, or C at the position corresponding to the degenerate (N) position that is degenerate in the composition, a mixture of all of the nucleotide precursors are added to the synthesis reaction such that all four nucleotides are randomly incorporated into the oligonucleotide at that position, simultaneously producing four different sequences, and preferably in equimolar amounts. However, less than all four common nucleotides can be used at an "N" position. Exemplary syntheses of degenerate oligonucleotides are described herein at Example 1.

C. Methods for Producing Oligonucleotides of Preselected Sequence

The invention contemplates methods for producing an oligonucleotide of preselected nucleotide sequence by combining the subunit oligonucleotides of a library described herein. The combining step generally involves ligation of two duplex DNA molecules having complementary cohesive (overhanging) termini, and having known nucleotide sequences. By selecting the duplex DNA molecules, or oligonucleotide subunits for assembling the duplexes, from a pre-made library, the method simplifies the process by eliminating the need for de novo chemical synthesis.

Thus, the invention describes a method in which oligonucleotides are selected from a library of this invention having sequences preselected to hybridize and form the desired ds DNA molecules. Thus, in this embodiment, the method comprises:

a) selecting at least one oligonucleotide member from a library of this invention;

b) hybridizing in an aqueous ligation buffer the oligonucleotide member(s) selected in step (a) having a preselected nucleotide sequence and capable of hybridizing to form a ligation reaction substrate; and c) ligating the ligation reaction substrate to form a ligation reaction product containing the oligonucleotide of preselected nucleotide sequence.

A ligation reaction substrate is a structure where the complementary overhangs of two (or more) ds DNA molecules (hybridized complexes) are hybridized so as to provide a 3'-hydroxylated terminus immediately adjacent to a 5'-phosphorylated terminus. A ligation reaction product is a ligation reaction substrate having had a ligation reaction performed between the adjacent 3'-hydroxylated terminus and the 5'-phosphorylated terminus resulting in a bond between the 3' and 5' termini. Where a ligase is used, the bond is a phosphodiester bond. An exemplary structure after ligation is shown in FIG. 1.

In a related embodiment, the method generally comprises the steps of:

a) providing in an aqueous ligation buffer an admixture of first and second double-stranded (ds) DNA molecules of preselected nucleotide sequence, each of said ds DNA molecules comprised of two hybridized oligonucleotides that form an overhang, said oligonucleotides having a length of at least 5 nucleotide bases, and the overhangs comprised of at least one nucleotide base, wherein the sequence of said first ds DNA overhang is complementary to the sequence of said second ds DNA overhang, to form a ligation reaction admixture;

b) hybridizing the overhangs of said first and second ds DNA molecules to form a ligation reaction substrate; and c) ligating said ligation reaction substrate to form a ligation reaction product containing said oligonucleotide of preselected nucleotide sequence.

Preferably the oligonucleotide provided in step (a) is 5 to 10 bases in length and the overhangs are from 1 to 3 bases in length, and more preferably the overhangs are 2 bases long.

In one embodiment, the invention contemplates the ligation of two duplexes having structures as described above and shown in FIG. 1.

Although the example shown in FIG. 1 illustrates a 5' overhang on both duplexes A and B, the invention can also be practiced with complementary 3' overhangs.

Extending the reaction scheme of FIG. 1, the present invention contemplates duplexes having at least one, and preferably 1 to 3, nucleotides in the complementary overhangs, although a two base overhang is preferred. Furthermore, the length of the oligonucleotide in the region of complementarity in a duplex is at least 5 nucleotides, and is preferably 5 to 10 nucleotides, although it is particularly preferred when the complementarity is formed by 5 to 6 nucleotides because of the resulting library size, as discussed further herein. Thus, the invention can utilize duplexes having one blunt end comprised of one the following pairs of oligonucleotide structures: duplexes having a one nucleotide overhang: 5mer/6mer, 6mer/7mer or 7mer/8mer; having a two nucleotide overhang: 5mer/7mer, 6mer/8mer or 7mer/9mer; or having a three nucleotide overhang: 5mer/8mer, 6mer/9mer or 7mer/10mer. Particularly preferred duplexes of this type are 5mer/7mer or 6mer/8mer duplexes.

In another embodiment, the duplexes can each have two overhangs as shown by 8mer/8mer duplexes illustrated in Schemes I and II. Thus, there is no requirement that one terminus of a duplex be blunt-ended as illustrated for the outside termini in the example shown in FIG. 1, so long as complementary overhangs are provided for ligation of two duplexes. A preferred duplex is the 8mer/8mer duplex having a 2 nucleotide overhang at each termini.

Insofar as hybridization occurs rapidly, the providing step (a) and the hybridizing step (b) can be performed simultaneously.

Ligation can be effected by any means that results in the formation of a bond between adjacent 3' hydroxyl and 5' hydroxy groups (or analogs) of adjacent oligonucleotides. These ligation means can include chemical or enzymatic methods. Particularly preferred enzymatic means are conducted by the use of bacteriophage T4 DNA ligase, as exemplified herein, which results in the formation of a phosphodiester bond.

In preferred embodiments, the overhang is a 5' overhang. In a particularly preferred embodiment, the 5' overhang of one duplex is phosphorylated.

Typically, the provided ds DNA molecules are selected from a library of ds DNA molecules as described herein.

In addition, rather than admixing duplex DNA molecules, the present method for producing an oligonucleotide of preselected nucleotide sequence can be practiced by providing oligonucleotides according to this invention having preselected nucleotide sequences as to form the above-defined duplexes having complementary termini.

Thus, the oligonucleotides forming the oligonucleotide components of the upstream and downstream duplexes can be added together to form a ligation reaction admixture in the form of single-stranded oligonucleotides or in the form of prehybridized duplexes.

In this single-stranded oligonucleotide embodiment, and using the 8mer/8mer duplex as exemplary, four 8mer oligonucleotides are added together to form a ligation reaction admixture. This embodiment is described in Example 5 herein. The admixed oligonucleotides first anneal to their respective complementary oligonucleotides to form the two (upstream and downstream) duplexes, such as the duplexes shown in the first step of Scheme I, and subsequently are ligated by DNA ligase to form a ligation product as described herein.

Similarly, two 6mer oligonucleotides and two 8mers oligonucleotides can be admixed to form two 6mer/8mer duplexes with complementary dinucleotide overhangs as seen for the duplexes in FIG. 1 .

Using the above outlined approaches for producing an oligonucleotide of predetermined nucleotide sequence, the present invention contemplates providing one or more libraries of oligonucleotides designed to allow the user to select specific oligonucleotides from the library to build a longer oligonucleotide of preselected sequence.

Thus in one embodiment, first and second oligonucleotides are provided that can hybridize to form a first duplex DNA, and third and fourth oligonucleotides are provided that can hybridize to form a second duplex DNA. The sequence of the four provided oligonucleotides are preselected as to form the first and second duplex DNA molecules such that they have complementary overhangs.

In one embodiment, a means for directing the hybridization of complementary overhangs is contemplated to selectively direct the hybridization of the desired overhangs. To that end, it is preferred to use combinations of nucleotide sequences in the two complementary overhangs that prevents self hybridization. This is accomplished by using sequences in the overhang which are not self-complementary. An example of self complementarity are the sequences AT, TA, GC and CG when present in an overhang. Where two duplex DNA molecules are to be ligated as shown in reaction Scheme I in which a duplex contains two overhangs, it is preferred required that the sequence of the overhangs be selected such that only one of the overhangs is complementary with the target overhang to which it is to be ligated, so as to minimize unwanted ligations.

In addition, hybridization direction can be affected by the kinetics of the reaction between complementary termini. For example, the use of molar excesses of one species, will favor hybridization between species rather than self hybridization of the minority species.

A preferred method comprises (1) selecting a first oligonucleotide from a first library defined by the formula YZ as defined previously, (2) phosphorylating the selected oligonucleotide, (3) admixing the phosphorylated oligonucleotide with a second and third oligonucleotide selected from a second library defined by the formula Z and a fourth oligonucleotide selected from the first library. The four oligonucleotides have preselected nucleotide sequences as to hybridize and form a ligation reaction substrate.

Alternatively, first, second and third libraries are provided: the first and second libraries having an oligonucleotide defined by the formula YZ as before, where oligonucleotides from the second library contain 5' phosphorylated termini, and the third library having an oligonucleotide defined by the formula Z. In this alternative, no phosphorylation step is required.

Although exemplary and preferred, the invention is not to be limited to the ligation of two duplexes (A and B; derived from Libraries A and B, respectively) having complementary overhangs as shown in FIG. 1. Also contemplated is the ligation of three or more duplexes, for example, duplexes A, B and C, each having overhangs adapted to direct the orderly assembly by hybridization and ligation of the three duplexes to form a ligated oligonucleotide. In this case, duplex B has a first and second overhang, duplex A comprises an overhang complementary to the first overhang of duplex B, and duplex C comprises an overhang complementary to the second overhang of duplex B. Furthermore, the overhang of C is not complementary to either first overhang of duplex B or to the overhang of duplex A, thereby minimizing unwanted hybridizations and ligations. A similar rationale is applied to the ligation of 4 or more duplexes according to the present invention.

In each case, the methods can be practiced by providing oligonucleotides into a hybridization admixture, or by providing pre-assembled duplexes and admixing the duplexes. Preferably, the methods are practiced by selecting oligonucleotides or duplexes from a library of this invention.

Thus the present invention contemplates the use of two distinct types of libraries: duplex DNA libraries and oligonucleotide libraries.

In another embodiment, the provided oligonucleotides having a 5' phosphate contains a thiol-phosphodiester linkage between the penultimate nucleotide and the 3' terminal nucleotide. The thiol linkage reduces the resulting ligated oligonucleotide's susceptibility to exonucleolytic degradation, increasing the lifetime of the oligonucleotide in primer extension reactions, or other applications where an exonuclease may be present.

In another embodiment the provided oligonucleotides are obtained by using degenerate oligonucleotide compositions in which the selected oligonucleotides for ligation are present as species in the degenerate oligonucleotide compositions. The compositions to be admixed for hybridization are selected to favor a single specific complement together with the other non-complementary oligonucleotides such that unwanted duplexes are selected against, thereby enriching for the production of a specific ligation reaction product. A preferred method uses the degenerate octanucleotide composition defined herein by the formula 5'-XXNXXNXX-3'.

In one embodiment, the method for producing an oligonucleotide of preselected nucleotide sequence comprises the steps of:

a) admixing first, second, third and fourth octanucleotide compositions to form a hybridization admixture, wherein each octanucleotide composition comprises octanucleotides according to the formula: 5'-XXNXXNXX-3' as defined earlier;

the first and second octanucleotide compositions are selected to contain sequences such that complementary hybridization of oligonucleotides of the first and second compositions forms a first double-stranded (ds) DNA molecule of the formula:

5'-P-XXNXXNXX-3'

3'-XXNXXNXX-5', the third and fourth octanucleotide compositions are selected to contain sequences such that complementary hybridization of oligonucleotides of the third and fourth compositions forms a second double-stranded (ds) DNA molecule of the formula:

5'-XXNXXNXX-3'
3'-XXNXXNXX-5', and wherein the first, second, third and fourth octanucleotide compositions are selected such that the first ds DNA molecule has a 5' overhang that is complementary to only one of the 5' overhangs present on the second ds DNA molecule;

b) hybridizing the octanucleotide compositions admixed in step (a) in an aqueous ligation buffer such that the complementary overhangs hybridize to form a ligation reaction substrate; and c) ligating the ligation reaction substrate to form a ligation reaction product containing the oligonucleotide of preselected nucleotide sequence.

In preferred embodiments using degenerate oligonucleotide compositions, the 5' terminus to be ligated on the overhang of the second ds DNA molecule is phosphorylated. The 5' terminal phosphate facilitates enzymatic ligation when using DNA ligase, and assures that the oligonucleotides of the complementary strand are not ligated (e.g., oligonucleotides A and C are ligated in Scheme II, whereas oligonucleotides B and D are not ligated).

The above method using degenerate oligonucleotide compositions need not be limited to using compositions containing the above-specified octanucleotide composition, as it is apparent to one skilled in the art that octanucleotide compositions based on a formula having the degenerate nucleotides "N" in positions other than $N_3, N_6$- may be utilized as described earlier. However, $N_3, N_6$- is particularly advantageous when using the 8mer/8mer format because all the "N's" are positioned across from "X's" such that complementary hybridization selects the appropriate hybridization partner in the duplex out of 16 possible different sequences.

A library of 4,096 9mer degenerate oligonucleotide compositions (members) could be formed using oligonucleotide compositions according to the compositional formula: 5'-XXNXXNNXX-3'. Such 9mers can be used to produce 18mers as follows:

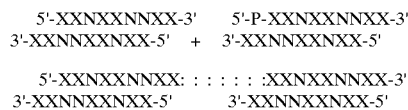

Alternatively, a library of 1024 7mers can be formed with the sequence 5'-XXNNXXX-3. Such 7mers can be used to produce 14mers as follows:

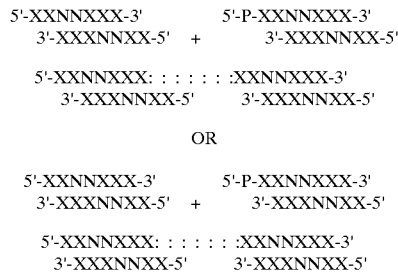

The particular advantage to using degenerate octanucleotides having two degenerate "N" nucleotides is that such a composition provides a collection of 16 unique species of octanucleotide, and because a library of this type of octanucleotide can contain every possible octanucleotide sequence by having 4,096 different compositions (families), each containing 16 different octanucleotides.

A library of 4,096 different compositions provides a manageable library size while at the same time provides materials sufficient to construct de novo, without chemical synthesis, a large diversity of oligonucleotides having a predetermined sequence OF LENGTH 16, 24, etc.

As a means for assisting the library user in the task of accessing the correct families of compositions for combination to construct by ligation a larger oligonucleotide, it is noted that the sequence of each oligonucleotide in a composition is known, and those sequence data can be stored, managed and sorted by automated means to provide rapid selection of appropriate compositions for building a preselected sequence.

Thus, a computerized computation system can be used to rapidly and easily identify appropriate compositions for admixture and ligation according to the present methods upon identifying the preselected oligonucleotide to be constructed by ligation.

Computers are particularly well suited for such automation, and can be used to support automated robotic systems for (1) maintaining a library, (2) selecting desired compositions upon instruction of a oligonucleotide primer to construct, and (3) admixing the biochemical reagents together with selected oligonucleotide compositions and carrying out the recited hybridization and ligation steps.

Hybridization of Oligonucleotides to Form a Ligation Reaction Substrate

A hybridization reaction mixture is typically prepared by admixing effective amounts of one or more oligonucleotide compositions of the present invention, and other components compatible with a hybridization reaction. These oligonucleotide compositions can contain two as DNA molecules having complementary overhangs, can contain three ds DNA molecules having complementary overhangs, or can contain degenerate or non-degenerate oligonucleotide compositions having sequences that, upon hybridization, form the requisite ds DNA molecules for ligation as described herein.

The hybridization reaction mixture is maintained in the contemplated method under hybridizing conditions for a time period sufficient for the oligonucleotides having complementarity to the predetermined sequence on corresponding complementary oligonucleotides to hybridize to those complementary nucleic acid sequences and form a hybridization product, i.e., first a ds DNA duplex, and then a ds DNA product having hybridized overhangs as shown in FIG. 1, FIG. 2, Scheme I or Scheme II.

The phrase "hybridizing conditions" when used with a maintenance time period, indicates subjecting the hybridization reaction admixture, in the context of the concentrations of reactants and accompanying reagents in the admixture, to time, temperature and pH conditions sufficient to allow one or more oligonucleotides to anneal with the complementary sequences present in the admixture, to form a nucleic acid duplex. Such time, temperature and pH conditions required to accomplish hybridization depend, as is well known in the art, on the length of the oligonucleotide to be hybridized, the degree of complementarity between the oligonucleotides (i.e., the length of complementary nucleotides in the sequence), the guanidine and cytosine content of the oligonucleotide, the stringency of hybridization desired, and the presence of salts or additional reagents in the hybridization reaction admixture as may affect the kinetics of hybridization. Methods for optimizing hybridization conditions for a given hybridization reaction admixture are well known in the art.

Typical hybridizing conditions include the use of solutions buffered to pH values between 4 and 9, and are typically carried out at temperatures from 0 degrees C. (0° C.) to 37° C., preferably about 2° C. to about 30° C., more preferably about 4° C. and for time periods from 0.5 seconds to 24 hours, preferably 2 minutes (min) to 1 hour. Exemplary are the conditions described in Examples 2 and 5.

Effective amounts of the oligonucleotides to be ligated that are present in the hybridization reaction admixture are generally well known and are typically expressed in terms of molar ratios between the oligonucleotides or duplexes to be hybridized. Preferred ratios are hybridization reaction mixtures containing from equimolar to ten-fold excess amounts of non-degenerate species to be hybridized. As is well known, deviations from equal molarity will produce hybridization reaction products. Thus although ratios where one of the two components (oligonucleotide A and oligonucleotide B or duplex A and duplex B as shown in FIG. 1) can be in as much as 100 fold molar excess relative to the other component, excesses of less than 50 fold, preferably less than 10 fold, and more preferably less the 2 fold are desirable in practicing the invention, except when degeneracies in one of the species to be hybridized necessitate the use of unequal molar ratios.

Effective concentrations of oligonucleotides in a hybridization reaction admixture are typically in the range of about 0.5 to 50 micromolar (uM), preferably about 1 to 10 uM, and more preferably about 5 uM.

In typical priming applications when using an oligonucleotide of this invention, the template is double-stranded, and therefore both the sense and anti-sense strands can potentially serve as template for a primer. Duplicate priming in a single sequencing reaction is undesirable because it produces unreadable sequencing ladders, and could potentially occur if certain oligonucleotides of the duplexes to be ligated (that are complementary to the desired oligonucleotide primer) are available for priming reactions on the template strand opposite to the strand to be sequenced.

For example, according to the scheme of FIG. 2, three products are formed in the ligation reaction: a 14mer, an 8mer and a 6mer. The 14mer is the desired primer. The 8mer could potentially act as a primer to the template strand complementary to the strand that the 14mer will prime in low temperature primer extension reactions, thus providing the unwanted duplicate priming. The 6mer could also theoretically prime, but is generally too short to initiate significant primer extension reactions. Thus it is desirable to block the capacity of the 8mer in this example to prime.

Thus, in one embodiment, it is preferred that the sequence of the oligonucleotide that provides the overhang and that is complementary to the final ligated oligonucleotide primer (e.g., the 8mer from duplex A derived from Library A in FIG. 2) has a 3' terminal nucleotide which is non-complementary to the sequence of its complementary oligonucleotide (e.g., the 6mer from duplex A derived from Library A in FIG. 2). In this situation, the 8mer from duplex A, which could otherwise provide a 3' terminus to initiate primer extension has a mismatch for the template to be extended at its 3' terminus, and thus cannot prime the template efficiently. Thus, the mismatch inhibits the 8mer from participating in a priming event.

With the design of a 3' mismatch as above, the ligation reaction product can be used directly in primer extension reactions where the 8mer from duplex A might prime without the need to purify the ligated oligonucleotide from the ligation reaction admixture.

Where the complementarity in the overhangs is selected to also be self-complementary, the use of unequal molar ratios can be utilized in one embodiment to favor hybridization and subsequent ligation of one pair over another. For example, referring to FIG. 2 that shows the hybridization of ds DNA molecules from library A and B, note that the sequence of the overhangs shown is self-complementary. To deter self-ligation of the ds DNA molecules from library B, a ten fold excess of library A molecules will favor A-B combinations over B-B combinations. A-A combinations are prevented due to the absence of a 5'phosphate on the terminus of the ds DNA molecule. Thus, the combination of molar ratio imbalances and phosphorylation of only one of the two species allows an effective and reproducible method for producing oligonucleotides according to the present methods. This embodiment is also described in the Examples.

Ligation of a Ligation Reaction Substrate to Form Oligonucleotide Primers of Preselected Sequence In producing a ligated oligonucleotide primer by the methods of this invention, the ligation reaction substrate is treated to ligation reaction conditions for a time period sufficient to form a phosphodiester bond between adjacent ligatable ends, namely between the 3' hydroxyl group at the 3'-terminus of oligonucleotide A and the 5' phosphate group at the 5'-terminus of oligonucleotide B. The product of an exemplary reaction is shown in FIG. 1, and in Schemes I and II.

The ligation step can be performed by any means available for forming a phosphodiester between the adjacent 5' and 3' termini, including enzymatic and chemical synthesis means. Preferred is the use of the enzyme ligase for catalytically inducing the ligation reaction.

Ligation reaction conditions are generally well known in the art and depend, in part, on the ligase to be used for forming the phosphodiester bond, and on the stability of the ligation reaction substrate.

A preferred ligase is bacteriophage T4 DNA ligase, such as is obtained from recombinant *Escherichia coli*, which can be obtained from a variety of commercial vendors.

Stability of the ligation reaction substrate is maintained by preserving hybridization reaction conditions during the manipulations after hybridization and during the ligation reaction. The substrate can vary in stability depending on the length of the hybridized oligonucleotide. For the shorter oligonucleotides contemplated by this invention, for example the hexameric oligonucleotides, it is preferred that hybridization and ligation reaction conditions be conducted below 30 degrees Centigrade (30° C.) and preferably between 4° C. and 22° C.

Ligation and hybridization can be accomplished in a single reaction step, and is preferred for convenience.

Ligation reaction conditions for ligation of the duplex DNA molecules typically require 0.5 to 100 uM of each primer, preferably about 10 to 50 uM, and more preferably about 20 uM primer which corresponds to about 500 nanograms (ng) of each oligonucleotide in a ligation reaction volume of 10 ul.

In one embodiment where the objective is to favor a preselected orientation of the ligated fragments rather than self-ligation, it is preferred to use about 5 to 10 fold molar excesses of the upstream (non-phosphorylated) duplex DNA molecule relative to the amount of the downstream duplex DNA molecule. Such a molar ratio reduces self-ligation of the downstream duplex DNA molecules. Other orientation-preference modifications can be utilized to further control the ligation reaction.

The ligation reaction conditions further require about 5 to 500 uM, preferably about 100 uM, rATP and 1x ligase buffer described herein. The ligation reaction admixture may also contains about 0 to 25 percent, preferably 7 to 12, more preferably 10 percent by weight, polyethylene glycol (PEG) 8000 because the PEG increases the rate of the ligation reaction. Other ligase buffers can be utilized, as is well known. The important factors in the present ligation method are the concentrations of the rATP and the input oligonucleotides, as described herein.

Ligase used in the present method is preferably T4 DNA ligase at a concentration of about 0.5 to 10, preferably about 1 to 5, Weiss units per 10 ul ligation reaction volume.

Hybridization and ligation reaction temperatures depend, as is known on the GC content of the oligonucleotide to be hybridized. For example, a hexanucleotide duplex comprised of all AT pairs require lower temperatures, typically below 22 degrees Centigrade (C.) and while a hexanucleotide of all GC pairs will hybridize and ligate up to about 37 degrees C. Thus the preferred range, depending on nucleotide content is about 4 to 30 degrees, preferably about 10 to 25 degrees, and more preferably 14 to 22 degrees C. Ligation reaction times can vary from about 0.5 min to 2 hours, although typically 5 min to 1 hour, and more preferably 5 to 15 minutes, are utilized.

Thereafter, the ligation reaction product formed is recovered, thereby producing the oligonucleotide of preselected nucleotide sequence. Typically, recovery comprises simply collecting the ligation reaction product and using it directly without further manipulations. Alternatively, the ligated oligonucleotide can be separated from the non-ligated precursor oligonucleotides, e.g., the 6mer and 8mer in the ligation product shown in FIG. 2. Separation techniques can include size separation or affinity isolation based on the presence of a terminal group such a biotin and the like and described further herein.

The resulting ligated oligonucleotide primer (ligation reaction product) formed by the action of the ligation reaction conditions on the ligation reaction substrate can be isolated from the other oligonucleotides in the ligation admixture or can be used directly as described further herein.

In preferred embodiments, the use of terminus modifications are contemplated that will control the ligation reaction and prevent unwanted ligations. An exemplary and preferred terminus modification is to phosphorylate the 5' terminus of the oligonucleotide to be ligated, but not phosphorylate the 5' terminus of the oligonucleotide in the complementary strand that participates in the overhang hybridization. See FIG. 1 for this example. The strategy provides at least two advantages.

First, the ligation reaction in this preferred strategy includes a 5'phosphate, and therefore, only the strand of choice is ligated, and not the oligonucleotides in the complementary strand. The result is that the non-ligated oligonucleotides are short relative to the ligated oligonucleotide. The short non-ligated oligonucleotides are generally too short to prime a PCR reaction or prime a DNA sequencing reaction. Therefore, it is not required that the non-ligated oligonucleotides be removed from the desired ligated oligonucleotide product prior to its use in PCR or sequencing reactions.

Second, insofar as 5' phosphate is required for enzymatic ligation by T4 DNA ligase, non-phosphorylated 5' termini cannot participate in self-ligations to form improper concatamers. Using FIG. 1 as an example, the ds DNA molecule from library A cannot form A-A ligations because the A molecule is not phosphorylated.

The optional separation of the oligonucleotide primer product from the shorter non-ligated oligonucleotides in a ligation reaction admixture can be accomplished by a variety of means following denaturation which destabilizes the hybridized duplexes. Exemplary separation methods include size fractionation of the oligonucleotides after denaturation of the ligation reaction product on gel sieve chromatography, on polyacrylamide gels and the like sizing methods.

Recovery of one strand from the duplex containing a ligation reaction product can be accomplished by a variety of means if desired, although selective recovery of the ligated oligonucleotide is not required for either PCR, sequencing or cycle-sequencing as shown in the Examples. Modification of either of the oligonucleotides before ligation to introduce a terminal group which affords selective retrieval of the desired oligonucleotide primer product is a preferred means for retrieval.

The biotin-avidin affinity system used for detection of non-isotopically labelled nucleotides is readily adapted to affinity based retrieval systems. In that system, biotin is introduced onto the 3' terminus of the downstream oligonucleotide or onto the 5' terminus of the upstream oligonucleotide which become incorporated into the ligated oligonucleotide product (e.g., the 3' terminus of the 8mer in library B or the 5' terminus of the 6mer in library A of FIG. 2). Thereafter, the presence of the biotin "tag" provides the means to selectively retrieve by elution the desired ligation reaction product.

The recovering step comprises the steps of admixing ligation reaction product having a biotin modified terminus with a suspension containing a solid phase comprising a solid support having avidin or streptavidin affixed thereto, to form an avidin binding admixture containing a liquid phase and a solid phase. Solid supports are generally well known, as are methods for fixing protein, such as avidin or streptavidin, to the solid support. Avidin or Streptavidin is available from a variety of commercial vendors.

The solid support can be in a variety of formats designed for easy recovery of the support away from the liquid phase to facilitate washing and eluting steps. These can take the form of beads, that can be physically separated based on size, by filtration or sedimentation. Alternatively, the solid support can have a functional property that makes separation simple, such as magnetism, or a biological binding affinity. Particularly preferred are magnetic beads that can be removed by magnetic fields.

The avidin binding admixture is then maintained under conditions compatible with a binding reaction between avidin and biotin for a time period sufficient for said avidin to bind to said biotin and form a biotin-avidin complex in the solid phase. The binding conditions are very flexible as the binding affinity between biotin and avidin is very high, and typically are aqueous solutions which do not denature DNA hybrids (duplex DNA). Time periods for binding are extremely fast, typically under one hour, and as fast as 1 to 10 minutes at room temperature.

The ligation reaction product is then eluted away from the solid phase to form the isolated oligonucleotide of preselected nucleotide sequence. Elution can be accomplished by any condition which disrupts (denatures) DNA duplexes to form single stranded oligonucleotides. Exemplary is the use of high temperature, e.g., greater than 65 degrees in 1x ligation buffer, or the like denaturing conditions, such as 0.1 to 0.5M NaOH.

Use in Directed Sequencing

Directed sequencing (primer walking) is a multi-step process in which a large sequence of nucleotides is determined by the steps of: (1) determining a first region of nucleotide sequence, (2) 5 preparing a sequencing primer based on the downstream 3' region of the determined sequence to design the sequencing primer as to be complementary to the template at that downstream region, (3) determining a second region of nucleotide sequence using the sequencing primer designed from the previously determined sequence in a primer extension-based sequencing procedure (e.g., dideoxy sequencing), and (4) repeating steps (2) and (3) for as many cycles as needed to walk down the entire sequence to be determined. This approach is termed directed sequencing because the choice of primer directs the subsequent sequencing steps and thereby sequentially orders the sequence information obtained. Directed sequencing is typically compared to and preferred over random sequencing methods where the sequence information obtained is not directed in any particular order.

In preferred embodiments for practicing the present methods as applied to directed sequencing, the use of the oligonucleotide compositions provide a particular advantage over previous directed sequencing methods.

For example, using previous techniques, after a region of nucleic acid sequence was determined, a new sequencing primer would be required to complete the next "directed" sequencing step. That required primer must be chemically synthesized, which consumes time and the expense of custom oligonucleotide synthesis.

By the present invention, the required sequencing primer can be constructed from a pre-existing "library" of oligonucleotide or duplex DNA compositions according to this invention by:

(1) selecting a nucleotide sequence in the region of the template for designing a directed sequencing primer, (2) selecting four oligonucleotide compositions (degenerate or non-degenerate) or two duplex DNA compositions from one or more libraries of the present invention, as needed, to produce an oligonucleotide having complementarity to the region of the template selected for directed sequencing, and (3) following the methods herein for admixing and ligating the selected compositions to form the oligonucleotide primers of preselected sequence. In the process of forming the ligated oligonucleotide primer, the resulting ligation reaction product is ready for sequencing without further manipulation. Exemplary is the ligation of non-degenerate oligonucleotides to form a 14mer oligonucleotide primer and sequencing of ssm13mp18 described in Example 2 and shown in FIG. 4. A further example is the ligation of degenerate oligonucleotides to form a 16mer primer and sequencing of template as described in Examples 6, 7 and 8.

The methods for producing ligated primers can be applied to a variety of methods for manipulating and analyzing nucleic acid molecules, as will be apparent to one skilled in the art.

For example, a ligation reaction product can be used in primer extension reactions to produce primer extension reaction products. After producing the ligation reaction product, the resulting oligonucleotide is used in a primer extension reaction to form a primer extension reaction product containing the ligated primer. By providing excess amounts, relative to template, of the oligonucleotide to a hybridization reaction one can cycle through successive rounds comprising (1) hybridization of the oligonucleotide primer, (2) primer extension, and (3) denaturation to remove the primer extension product. By doing so the excess oligonucleotides will repeatedly hybridize to the template and extend to cyclically produce primer extension product. This process is referred to as cycle-extending because repeated primer extension product is formed by cycling through the above steps.

In cycle-extending, the denaturation step is typically a heat treatment manipulation to melt the duplex DNA. Such heat treatment necessitates that the polymerase used in the primer extension step be heat stable, or that additional polymerase be added to each primer extension reaction admixture at each cycle. The primer extension step in cycle-extending is preferably conducted with a heat stable polymerase as described herein for the polymerase chain reaction (PCR) methods.

In a related embodiment, chain terminators such as are used in dideoxy sequencing reaction can be used in the primer extension step of the above cycle-extending method. This allows the repeated production of sequencing reaction products in a cycle-sequencing method. By including the reagents normally used in a dideoxy sequencing reaction at the primer extension step, one can produce amounts of sequencing reaction product in excess of the amount normally provided after one dideoxy sequencing reaction, thereby increasing the sensitivity of the normal sequencing reaction. An exemplary cycle-sequencing procedure is described in Example 4.

Use in PCR Reactions

Polymerase chain reactions (PCR) utilize primer extension primers in a pairwise array as is well known. The PCR reaction, however, consumes mass quantities of the primers as each primer becomes incorporated in the primer extension product at each PCR cycle. Therefore, the present oligonucleotide libraries and methods are particularly well suited to solving the problem of PCR primer preparation insofar as the PCR primers can be synthesized by ligation as described herein from the pre-existing libraries of this invention rather than chemically synthesized de novo.

For example, to conduct a PCR reaction on a DNA sequence, one selects the desired PCR primer pair, and determines for each primer, the 3' primer and the 5' primer, which oligonucleotides of preselected sequence to produce, using the present methods. Thereafter, one admixes the prepared oligonucleotide compositions with a target for PCR amplification to form a PCR reaction admixture, ready for the PCR reaction.

Other permutations on PCR reaction methodologies will readily be apparent to one skilled in the art.

PCR amplification methods are described in detail in U.S. Pat. Nos. 4,683,192, 4,683,202, 4,800,159, and 4,965,188, and at least in several texts including "PCR Technology: Principles and Applications for DNA Amplification", H. Erlich, ed., Stockton Press, New York (1989); and "PCR Protocols: A Guide to Methods and Applications", Innis et al., eds., Academic Press, San Diego, Calif. (1990).

The PCR reaction is performed by mixing the PCR primer pair, preferably a predetermined amount thereof, with the template nucleic acid having the sequence to be amplified, preferably a predetermined amount thereof, in a PCR buffer to form a PCR reaction admixture. The admixture is maintained under polynucleotide synthesizing conditions for a time period, which is typically predetermined, sufficient for the formation of a PCR reaction product, thereby producing an amplified PCR reaction product.

The PCR reaction is performed using any suitable method. Generally it occurs in a buffered aqueous solution, i.e., a PCR buffer, preferably at a pH of 7–9, most preferably about 8. Preferably, a molar excess (for genomic nucleic acid, usually about $10^6$:1 primer:template) of the primer is admixed to the buffer containing the template strand. A large molar excess is preferred to improve the efficiency of the process.

The PCR buffer also contains the deoxyribonucleotide triphosphates DATP, dCTP, dGTP, and dTTP and a polymerase, typically thermostable, all in adequate amounts for primer extension (polynucleotide synthesis) reaction. The resulting solution (PCR admixture) is heated to about 90° C.–100° C. for about 1 to 10 minutes, preferably from 1 to 5 minutes. After this heating period the solution is allowed to cool to 35° to 60° C., and preferably 40° to 50° C. depending upon the actual base composition as is known, which is preferable for primer hybridization. The synthesis reaction may occur at from room temperature up to a temperature above which the polymerase (inducing agent) no longer functions efficiently. Thus, for example, if DNA polymerase is used as inducing agent, the temperature is generally no greater than about 40° C. An exemplary PCR buffer comprises the following: 50 mM KCl; 10 mM Tris-HCl; pH 8.3; 1.5 mM $MgCl_2$; 0.001% (wt/vol) gelatin, 200 $\mu$M dATP; 200 $\mu$M dTTP; 200 $\mu$M dCTP; 200 $\mu$M dGTP; and 2.5 units Thermus aquaticus DNA polymerase I (U.S. Pat. No. 4,889,818) per 100 microliters of buffer. Other exemplary PCR reactions are described in Example 3.

The inducing agent may be any compound or system which will function to accomplish the synthesis of primer extension products, including enzymes. Suitable enzymes for this purpose include, for example, E. coli DNA polymerase I, Klenow fragment of E. coli DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of each primer and proceed in the direction of 5' to 3' along the template strand, until synthesis terminates, producing molecules of different lengths. There may be inducing agents, however, which initiate synthesis at the 5' end and proceed in the above direction, using the same process as described above.

The inducing agent also may be a compound or system which will function to accomplish the synthesis of RNA primer extension products, including enzymes. In preferred embodiments, the inducing agent may be a DNA-dependent RNA polymerase such as T7 RNA polymerase, T3 RNA polymerase or SP6 RNA polymerase. These polymerases produce a complementary RNA polynucleotide. The high turn over rate of the RNA polymerase amplifies the starting polynucleotide as has been described by Chamberlin et al., *The Enzymes*, ed. P. Boyer, PP. 87–108, Academic Press, New York (1982). Another advantage of T7 RNA polymerase is that mutations can be introduced into the polynucleotide synthesis by replacing a portion of cDNA with one or more mutagenic oligodeoxynucleotides (polynucleotides) and transcribing the partially-mismatched template directly as has been previously described by Joyce et al., *Nucleic Acid Research*, 17:711–722 (1989). Amplification systems based on transcription have been described by Gingeras et al., in *PCR Protocols, A Guide to Methods and Applications*, pp 245–252, Academic Press, Inc., San Diego, Calif. (1990).

If the inducing agent is a DNA-dependent RNA polymerase and therefore incorporates ribonucleotide triphosphates, sufficient amounts of ATP, CTP, GTP and UTP are admixed to the primer extension reaction admixture and the resulting solution is treated as described above.

PCR is typically carried out by thermocycling i.e., repeatedly increasing and decreasing the temperature of a PCR reaction admixture within a temperature range whose lower limit is about 10° C. to about 40° C. and whose upper limit is about 90° C. to about 100° C. The increasing and decreasing can be continuous, but is preferably phasic with time periods of relative temperature stability at each of temperatures favoring polynucleotide synthesis, denaturation and hybridization.

D. Oligonucleotide Library Kits

Many of the reagents described herein (e.g., nucleic acids such as the oligonucleotides and duplex DNA molecules in a library of this invention) have a number of forms, particularly variably protonated forms. As the skilled practitioner will understand, representation herein of one form of a compound or reagent is intended to include all forms thereof.

The reagents described herein can be packaged in kit form. As used herein, the term "package" refers to a solid matrix or material customarily utilized in a system and capable of holding within fixed limits one or more of the reagent components for use in a method of the present invention. Such materials include glass and plastic (e.g., polyethylene, polypropylene and polycarbonate) bottles, vials, paper, plastic and plastic-foil laminated envelopes and the like. Thus, for example, a package can be a glass vial used to contain the appropriate quantities of oligonucleotide compositions, restriction enzyme(s), DNA polymerase, polynucleotide ligase, or a combination thereof. An aliquot of each component sufficient to perform at least one ligation reaction will be provided in each container.

A particularly preferred kit contains a library of the present invention together with a polynucleotide ligase, such as DNA ligase.

Kits useful for producing a preselected primer for sequencing of a specific nucleic acid sequence or for conducting a PCR amplification reaction using a primer extension reaction methodology also typically include, in separate containers within the kit, dNTPs where N is adenine, thymine, guanine and cytosine, and other like agents for performing sequencing reactions.

The reagent species of any system described herein can be provided in solution, as a liquid dispersion or as a substantially dry powder, e.g., the oligonucleotides may be provided in lyophilized form.

In one embodiment, the present invention contemplates a kit for producing an oligonucleotide of preselected priming specificity, which kit comprises a plurality of separate packages (containers) within an enclosure, each package containing a different oligonucleotide or duplex DNA molecules composition according to this invention.

Kits having a plurality of such compositions are also referred to herein as libraries.

In one embodiment a preferred library contains up to 4096 separate containers, each containing a different 8mer as defined herein, where each 8mer in the library has the same dinucleotide sequence at its 5' terminus. In a related embodiment a library contains up to 4096 separate containers, each containing a different duplex DNA molecule comprised a 6mer/8mer oligos, where each 8mer has the same dinucleotide sequence at its 5' terminus. Exemplary is the library shown in FIG. 4.

Alternatively, a preferred library contains 4,096 containers each containing a different degenerate octanucleotide composition as defined herein. Particularly preferred is a library where each degenerate octanucleotide composition has octanucleotides according to the formula 5'-XXNXXNXX-3' as described herein.

In another embodiment, a kit comprises two libraries, a first having a shorter oligonucleotide and a second having a longer oligonucleotide according to the formula YZ as described before, where the shorter oligonucleotide is complementary to the sequence Z. Exemplary is a kit having a first library of 6mers, and a second library of 8mers, as described herein. optimally, the 8mer library is phosphorylated at the 5' termini.

The oligonucleotides of the first and second libraries have sequences such that the complementary hybridization of a member of the first library with a member of the second library forms a double-stranded DNA molecule having at least a one nucleotide base overhang of the second library oligonucleotide sequence, and such that the terminal nucleotide(s) of all oligonucleotides in the second library that form the overhang have the same nucleotide sequence. Preferably, the overhang formed by complementary hybridization is a 5' terminal overhang, and more preferably the overhang is a dinucleotide sequence selected from the group consisting of GG, CC, TT, AA, TC, CT, GA, AG, TG, GT, AC, CA, NI and IN, wherein N is selected from the group consisting of A, T, G and C, and wherein I is inosine.

Alternatively, a kit comprises three libraries, namely a 6mer, an 8mer, and an 8mer that is phosphorylated at their 5' termini. This kit provides all the materials to assemble a pair of duplexes A and B without the need for the manipulative step of phosphorylation.

Preferred kits contain organized enclosures such that the different oligonucleotides are distributed in a preselected array. For example, a 96-well microtiter tray is an enclosure that provides an array of 96 containers (wells). A larger library can be comprised of a series of microtiter trays, such as is shown in FIG. 2. Such organized arrays provides a convenient and manageable way to identify and access the different members of the library, and is amenable to automated processes for oligonucleotide synthesis according to the present methods.

EXAMPLES

The following examples are intended to illustrate, but not limit, the present invention.

1. Oligonucleotide Synthesis

Most of the oligonucleotides in the Examples were synthesized from the 3' end on an Applied Biosystems Inc. (ABI) DNA synthesizer, model 391 or 392, with ABI reagents at a 0.2 um scale using standard protected nucleotide cyanoethyl phosphoramidite chemistry and deprotection protocols according to the manufacturer's instructions.

Where there is a oligonucleotide composition having a common position (N) that is degenerate, a mixture of all four phosphoramidites was used to extend the growing nucleotide polymer by the addition of any one of the four bases (A, C, G, or T). All oligonucleotides are written herein in the standard 5' to 3' orientation.

The oligonucleotides were chemically phosphorylated where appropriate at their 5'-end by is the addition, and subsequent deprotection of, 1-Dimethoxytrityl-2,2'-sulfonyldiethanol-1-CED™ phosphoramidite (ABI). In an alternate procedure, oligonucleotides were phosphorylated by the use of T4 polynucleotide kinase.

The crude oligonucleotides were purified by PAGE and then desalted and lyophilized by standard procedures.

Some of the oligonucleotides used in the Examples are described in Table 1:

TABLE 1

| Oligo No. | N-mer | Sequence |
|---|---|---|
| 1 | 6 | 5'-ACGACG-3' |
| 2 | 8 | 5'-GCCGTCGT-3' |
| 3 | 8 | 5'-P-GCCAGTGC-3'[a] |
| 4 | 6 | 5'-GCACTG-3' |
| 5 | 14 | 5'-ACGACGGCCAGTGC-3'[b] (SEQ ID no: 1) |
| A' | 19 | 5'-TAAAACGACGACGGCCAGT-3' (SEQ ID no: 3) |
| B | 22 | 5'-TGATTCCAACGAGGAAAGCACG-3' (SEQ ID no: 4) |

[a]Oligonucleotide No. 3 is shown with a phosphate group at its 5' terminus.
[b]The sequence of oligonucleotide No. 5 shows the product of ligation of oligonucleotide Nos. 1 and 3, and is aligned over oligonucleotide A' to illustrate the common sequences.

2. Ligation of Oligonucleotides to Form a Ligation Reaction Product

The oligonucleotides Nos. 1, 2, 3 and 4 shown in Table 1 were synthesized, and oligonucleotide No. 3 was chemically phosphorylated on its 5' terminus, as described in Example 1. The oligonucleotides Nos. 1, 2, 3 and 4 so produced were admixed into a ligation reaction admixture containing the following in 1X ligation buffer (50 mM Tris-HCl, pH 7.5, 7 mM MgCl$_2$, 1 mM DTT) : 10% PEG 8000, 100 uM rATP, 5 uM of each of oligonucleotides Nos. 1, 2, 3 and 4, and 4 units of T4 DNA ligase. The ligation reaction admixture was then maintained (incubated) at 14° C. for 60 minutes to allow the oligonucleotides to anneal to their complements to form duplexes, for the cohesive overhangs to hybridize, and for the ligation reaction to occur and form a ligation reaction product comprising a 14mer hybridized to oligonucleotide Nos. 2 and 4. The reaction scheme is shown in FIG. 1.

When analyzed on a 20% denaturing acrylamide gel, greater than 90% ligation efficiency was observed in the presence of ligase, whereas only nonligated oligonucleotides were observed in the absence of ligase. Similar ligation reactions conducted at 14° C. were greater than 90% complete after 5 minutes, and greater that 99% complete after 15 minutes.

In an alternate procedure, oligonucleotide No. 3 was phosphorylated by the use of T4 DNA kinase.

3. Ligation Reaction Product as a Polymerase Reaction Primer

The 14mer oligonucleotide ligation reaction product produced in Example 2 was used directly, without purification from the ligation reaction admixture, as a polymerase chain reaction (PCR) primer. To that end, a PCR admixture was prepared by admixing the following in 1X PCR buffer (10 mM Tris-HCl, pH 8.3, 50 mM KCl, 4 mM MgCl$_2$, 0.1% gelatin): 250 uM dATP, 250 uM dGTP, 250 uM dTTP, 250 uM dCTP, 5 ng ssM13mp18 template DNA, 200 ng of oligonucleotide No. B (22mer), either 200 ng of oligonucleotide No. A' (19mer) or 300 ng of ligation reaction product (14mer) produced in Example 2, and 1 unit Taq DNA polymerase.

The PCR admixture was then cycled in a 9600 Gene Amplification System PCR thermocycler (Perkin Elmer Cetus) under the following conditions: first, the admixture was maintained at 95° C. for 5 minutes, next the admixture was cycled through the following three temperatures at the indicated times for 25 cycles: 95° C. for 1 min, 40° C. for 1 min, and 72 ° C. for 1.5 min; thereafter, the admixture was maintained at 72° C. for 5 minutes to form a PCR product.

The resulting PCR product was analyzed by gel electrophoresis on a 1% agarose gel, the electrophoresed gel was stained with ethidium bromide, and the electrophoresed PCR products were visualized using ultraviolet light. The PCR reaction scheme and the gel analysis results are shown in FIG. 3.

Based on the template (ssM13mp18) sequence and the choice of PCR primers, a 980 base pair (bp) fragment is expected to be amplified by the use of either of the primer pairs B/A or B/A', where A is the 14mer ligation reaction product formed in Example 2, and A' is the control 19mer. An amplified 980 bp PCR product is observed when either the control 19mer/22mer (lane 1) or ligation reaction product 14mer/22mer (lane 2) primer pairs were used, indicating that a ligation reaction product formed by the present methods is able to prime template accurately in a PCR reaction when added to the PCR admixture as unpurified ligation reaction product. No PCR product is formed when ligase is not added to the ligation reaction admixture (lane 3) indicating that 6mers and 8mers are not able to prime in a PCR reaction under the conditions tested.

4. Cycle-Sequencing Using a Ligation Reaction Product as Primer

The 14mer oligonucleotide in the ligation reaction product formed in Example 2 was used to prime a DNA sequencing reaction, in a cycle-sequencing format. To that end, a sequencing reaction admixture was prepared by admixing the following in 1X sequence buffer (10 mM Tris-HCl, pH 8.3, 50 mM KCl, 4 mM MgCl$_2$, 0.1% gelatin): 0.5 uM DATP, 180 uM ddTTP, 5 uM dGTP, 30 uM ddGTP, 5 uM dTTP, 300 uM ddTTP, 5 uM dCTP, 180 uM ddCTP, 10 uCi α$^{33}$P-dATP (1332 Ci/mmole; 10 uCi/ml; New England Nuclear), 100 ng ssM13mp18 template DNA, either 10 ng of oligonucleotide No. A' (19mer) or 10 ng of ligation reaction product (14mer) produced in Example 2, and 1 unit Taq DNA polymerase.

The sequencing reaction admixture was then cycled in a 9600 Gene Amplification System PCR thermocycler (Perkin Elmer Cetus) under the following conditions: first, the admixture was maintained at 95° C. for 5 minutes, next the admixture was cycled through the following three temperatures at the indicated times for 30 cycles: 95° C. for 10 seconds, 50° C. for 20 seconds, and 72° C. for 30 seconds; thereafter, the admixture was maintained at 72° C. for 5 minutes to form a cycle-sequencing reaction product. The sequencing reaction was stopped by the addition of 5 uL of stop dye mix (90% formamide, 0.05% bromophenol blue, 0.05% xylene cyanol), and 2 ul was electrophoresed on a 6% acrylamide/7M urea sequencing gel.

Figure 4:
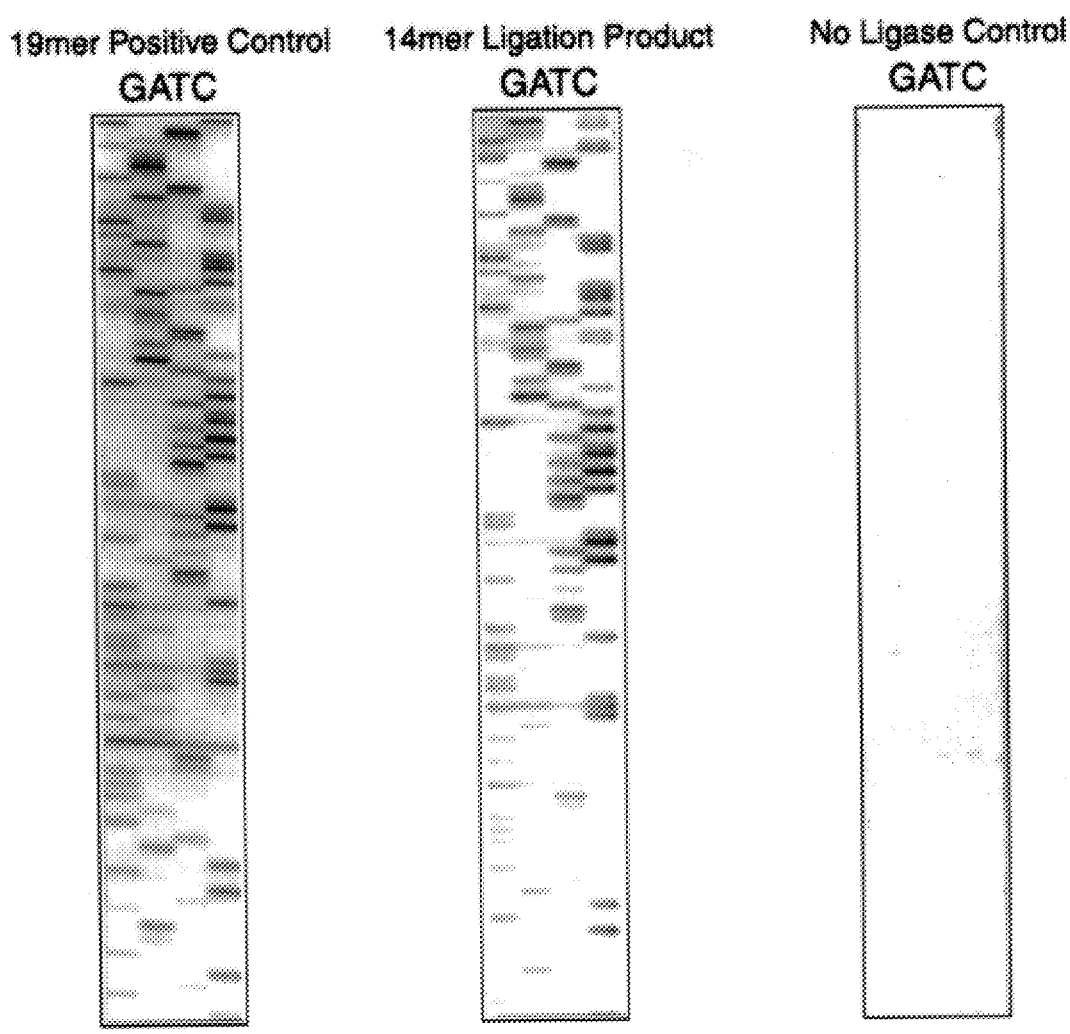
FIG. 4 illustrates the sequencing results of cycle-sequencing ssm13mp18 using an oligonucleotide 14mer primer produced as described in Example 4. The left panel shows a sequencing gel profile produced using the chemically synthesized 19mer positive control (Primer A'), the center panel shows a sequencing gel profile produced using the 14mer ligation product (primer A), and the right panel shows a sequencing gel profile produced using the ligation 25 reaction product when no ligase is added to the ligation reaction.

The results of the sequencing gel analysis is shown in FIG. 4. The 14mer ligation reaction product in unpurified form specifically primed a unique sequence ladder using the ssM13mp18 template, as shown in the center panel of FIG. 4. The sequence ladder produced by a chemically synthesized 19mer (oligonucleotide A') primer was indistinguishable (left panel of FIG. 4) from the ladder formed by the ligation reaction product, indicating that primer produced by the present methods efficiently primes sequencing reactions. In the absence of ligase, no sequence ladder is seen (right panel) indicating that 6mers and 8mers do not significantly prime a sequencing reaction under the conditions utilized.

5. Ligation of Degenerate Oligonucleotides to Form a Ligation Reaction Product Ligation of degenerate oligonucleotide compositions was compared to ligation of a homogeneous (non-degenerate) oligonucleotide composition to determine if the resulting ligation reaction products can be reproducibly prepared. Oligonucleotide primer sets 6, 6n, 7, 7n, 8, and 8n described herein are shown in Table 2. Using primer sets 7 and 7n as exemplary of the primer sets, the oligonucleotide Nos. 7A, 7B, 7C, 7D (primer set 7) and the corresponding degenerate oligonucleotides 7An, 7Bn, 7Cn, and 7Dn (primer set 7n) having sequences shown in Table 2 were synthesized, and oligonucleotide Nos. 7C and 7Cn were chemically phosphorylated on their 5' termini, essentially as described in Example 1 except that they were produced commercially by Genosys, Inc. (The Woodlands, Tex.).

TABLE 2

| Oligo No. | N-mer | Sequence |
|---|---|---|
| 6 | 16 | 5'-AAACCCGACAGGACTA-3' (SEQ ID no: 5) |
| 6A | 8 | 5'-AAACCCGA-3' |
| 6An[a] | 8 | 5'-AANCCNGA-3' |
| 6B | 8 | 5'-TGTCGGGT-3' |
| 6Bn | 8 | 5'-TGNCGNGT-3' |
| 6C | 8 | 5'-P-CAGGACTA-3' |
| 6Cn | 8 | 5'-P-CANGANTA-3' |
| 6D | 8 | 5'-CCTAGTCC-3' |
| 6Dn | 8 | 5'-CCNAGNCC-3' |
| 7 | 16 | 5'-GGTAACTATCGTCTTG-3' (SEQ ID no: 6) |
| 7A | 8 | 5'-GGTAACTA-3' |
| 7An | 8 | 5'-GGNAANTA-3' |
| 7B | 8 | 5'-GATAGTTA-3' |
| 7Bn | 8 | 5'-GANAGNTA-3' |
| 7C | 8 | 5'-P-TCGTCTTG-3' |
| 7Cn | 8 | 5'-P-TCNTCNTG-3' |
| 7D | 8 | 5'-CCCAAGAC-3' |
| 7Dn | 8 | 5'-CCNAANAC-3' |
| 8 | 16 | 5'-TTTTCTACGGGGTCTG-3' (SEQ ID no: 7) |
| 8A | 8 | 5'-TTTTCTAC-3' |
| 8An | 8 | 5'-TTNTCNAC-3' |
| 8B | 8 | 5'-CCGTAGAA-3' |
| 8Bn | 8 | 5'-CCNTANAA-3' |
| 8C | 8 | 5'-P-GGGGTCTG-3' |
| 8Cn | 8 | 5'-P-GGNGTNTG-3' |
| 8D | 8 | 5'-AGCAGACC-3' |
| 8Dn | 8 | 5'-AGNAGNCC-3' |

[a]The "n" designates the oligonucleotide as being a degenerate oligonucleotide composition, having all four nucleotides (A, T, G and C) at the position indicated by "N" as described herein.

The oligonucleotides so produced were admixed into a 10 microliter (ul) ligation reaction admixture containing 1X ligation buffer (50 mM Tris-HCl, pH 7.5, 7 MM MgCl$_2$, 1 mM DTT), 100 uM rATP, 125 nanograms (ng) each of non-degenerate oligonucleotides A, B, C and D or 625 ng of degenerate oligonucleotides An, Bn, Cn and Dn, and 4 units of T4 DNA ligase. The ligation reaction admixture was first incubated on ice (0° C.) for 30 min, then maintained (incubated) at 65° C. for 5 minutes. The oligonucleotides thereby anneal to complementary sequences to form duplexes, the cohesive overhangs in the duplexes hybridize, and the ligation reaction proceeds to form a ligation reaction product comprising a 16 mer hybridized to oligonucleotide Nos. A and C. Scheme I shows the use of non-degenerate oligonucleotides, and the corresponding Scheme II shows the use of degenerate oligonucleotides. Note that where degenerate oligonucleotides are used, only specific complementary oligonucleotides participate in the hybridization, and corresponding degenerate non-complementary oligonucleotide species of the oligonucleotide composition do not participate in hybridization.

The ligation reaction products produced using primer sets 7 or 7n were analyzed by labeling an aliquot of the ligation reaction admixture with $^{33}$P-ATP and T4-polymucleotide kinase. Thereafter, the labeled products were loaded and electrophoresed on a 20% acrylamide/7M urea (denaturing) gel prepared in 1X TBE, and run at 60 watts (W) constant power, greater than 90% ligation efficiency was observed in the presence of ligase when non-degenerate oligonucleotides were used, whereas only nonligated oligonucleotides were observed in the absence of ligase. Similarly, a detectable amount of ligation occurred where degenerate oligonucleotides were used.

6. Degenerate Oligonucleotide Ligation Reaction Product as a Cycle Sequencing Reaction Primer The degenerate oligonucleotide ligation reaction product produced in Example 5 from primer set 7n was used directly, without purification from the ligation reaction admixture, as a primer for cycle sequencing of the pBluescript® plasmid IISK+. To that end, cycle sequencing was performed using the Cyclist™ DNA Sequencing Kit (Stratagene). Two ul of the ligation reaction admixture, or 5 ng of synthesized 16mer (oligonucleotide 7) were used to sequence 300 ng of pBluescript® plasmid IISK+.

Figure 5:
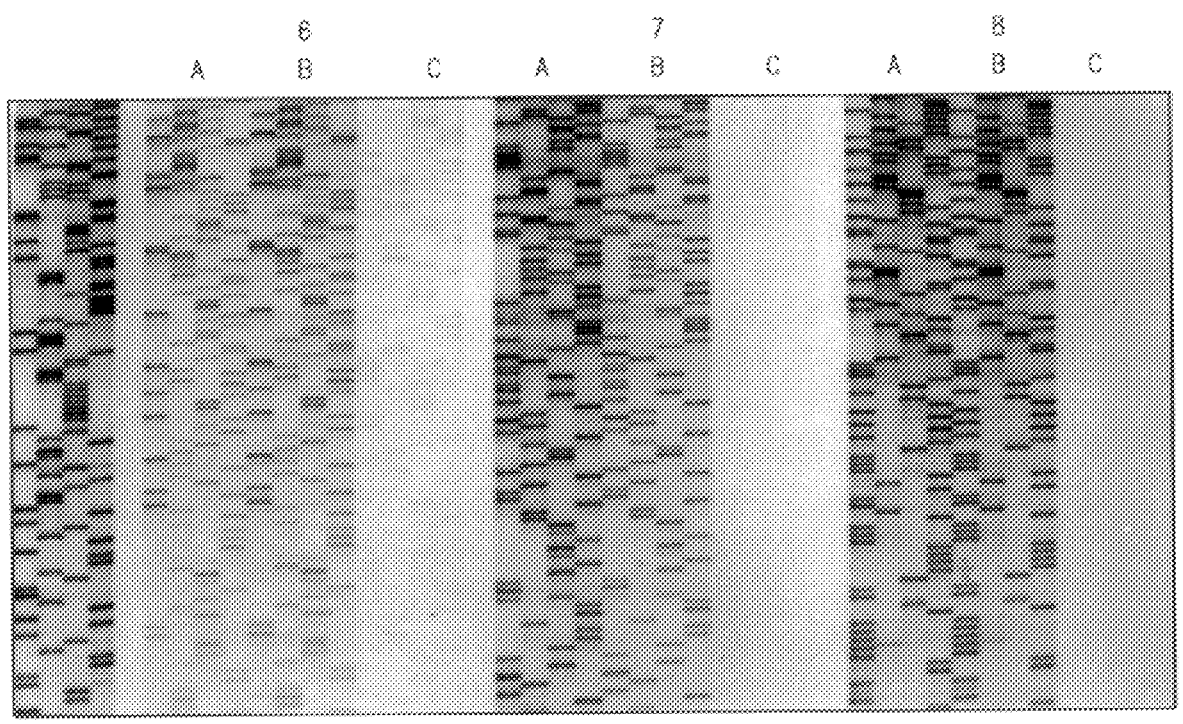
FIG. 5 illustrates the sequencing gel results of cycle-sequencing pBluescript® plasmid using a 16mer oligonucleotide primer produced as described in Example 6 by ligation of degenerate oligonucleotide compositions. Sequencing results are shown using the primers in primer set 6 described in Table 2, in 12 consecutive lanes, where the four lanes labeled 6A illustrate sequencing with a chemically synthesized positive control 16mer primer (oligonucleotide 6), the four lanes labeled 6B illustrate sequencing with the ligation reaction product produced from ligation of degenerate oligonucleotides 6An, 6Bn, 6Cn and 6Dn, and the four lanes labeled 6C illustrate sequencing with the same degenerate oligonucleotides without ligase added to the ligation reaction. Similar 12 lanes A, B and C are shown for sequencing results using primer set 7n and for primer set 8n. A control sequencing ladder is shown in four lanes on the extreme left of the Figure using a universal primer (1) for sequencing pBluescript® plasmid.

The cycle sequencing reaction admixture contained 10 mM Tris-HCl, pH 8.8, 50 mM KCl, 4 mM $MgCl_2$, 0.001% gelatin, 2 uM dATP, 5 uM dGTP, 5 uM dTTP, 5 uM dCTP, 10 microcuries (uCi) of $\alpha^{33}$P-dATP (1332 Ci/mmole; 10 uCi/ml; New England Nuclear), 2 units of Taq DNA polymerase, and one of the following; 180 uM ddATP, 180 uM ddCTP, 30 uM ddGTP or 300 uM ddTTP. The reaction admixture was initially denatured at 95° C. for 5 min, and then was cycled 30 times in a 9600 Gene Amplification System PCR thermocycler (Perkin Elmer Cetus) through a profile of 95° C. for 20 seconds, 50° C. for 30 seconds, and 72° C. for 40 seconds. Thereafter, 5 ul of stop dye (95% formamide, 20 mM EDTA, 0.05% bromophenol blue, 0.05% xylene cyanol) were added the admixture, and 2 ul of the resulting admixture were loaded and electrophoresed on 6% acrylamide/7M urea sequencing gel at a constant power of 60 watts. oligonucleotide primer sets 6, 6n, 8 and 8n were similarly prepared from the oligonucleotides shown in Table 2, ligated as in Example 5 and used in cycle sequencing as described above for primer sets 7 and 7n, and the sequencing results analyzed on sequencing gels. The sequencing gel results are shown in FIG. 5.

The results show that the sequencing ladder (four lanes corresponding to A, T, G and C) produced by three different degenerate oligonucleotide primers (shown in the B lanes for primer sets 6n, 7n or 8n) upon ligation according to the present methods is essentially indistinguishable from the sequencing ladder produced by using a synthetic 16mer primer (shown in the A lanes for oligonucleotides 6, 7 or 8), indicating that the primer produced by the present methods efficiently primes a cycle sequencing reaction without undesirable interfering reaction. In the absence of added ligase (shown in the C lanes), no sequencing ladder is seen indicating that the non-ligated 8mers of the degenerate oligonucleotide composition do not significantly prime the cycle sequencing reaction.

7. Reverse Transcriptase Sequencing Using a Degenerate Oligonucleotide Ligation Reaction Product as Primer The oligonucleotide in the ligation reaction product formed by using degenerate primer set 7n was used to prime a DNA sequencing reaction, in a reverse transcriptase (RT) sequencing format. To that end, a 10 ul RT sequencing reaction admixture was prepared by first admixing the following: 1 ul 10X reverse transcriptase buffer (50 mM Tris-HCl, pH 8.3, 20 mM KCl, 10 mM $MgCl_2$), 800 ng single-stranded pbluescript® plasmid II SK+ DNA (+ strand), 2 ul containing ligation reaction product from primer set 7 or 7n, or 5 ng of 16mer control oligonucleotide 7 (SEQ ID NO 6) and sufficient distilled water to bring the volume to 10 ul. This first admixture was incubated for 2–3 min at 50° C. Thereafter, 2.5 ul of label mix was added containing 5 uCi $\alpha^{33}$P-dATP (1332 Ci/mmole; 10 uCi/ml; New England Nuclear), 2 uM dCTP, 2 uM dGTP, 2 uM dTTP and 5 units avian myeloblastosis virus (AMV) reverse transcriptase (Stratagene), to form an RT labeling reaction admixture. The admixture was incubated 3–5 min at 50° C. to form labeled reaction product, and then 2.5 ul of the labeled reaction product was transferred to a fresh prewarmed (37° C.) tube containing 2.5 ul of one of the four ddNTP mixes (Sequenase Kit) and 0.5 units of Sequenase diluted in enzyme dilution buffer (10 mM Tris-HCl, pH 7.5, 5 mM DTT, 0.5 mg/ml BSA) to form an RT sequencing reaction admixture. The ddNTP mix contains 80 uM dATP, 80 uM dCTP, 80 uM dGTP, 80 uM dTPP, 50 uM NaCl, and 8 uM of one of the ddNTPs. The RT sequencing reaction admixture was incubated 3–5 min at 37° C., and then 4 ul of stop solution (95% formamide, 0.025% bromophenol blue, 0.025% xylene cyanol) was added to the incubated admixture. Two ul of the resulting RT sequencing reaction admixture were loaded onto and electrophoresed on a sequencing gel as described in Example 3 for cycle sequencing.

Figure 6:
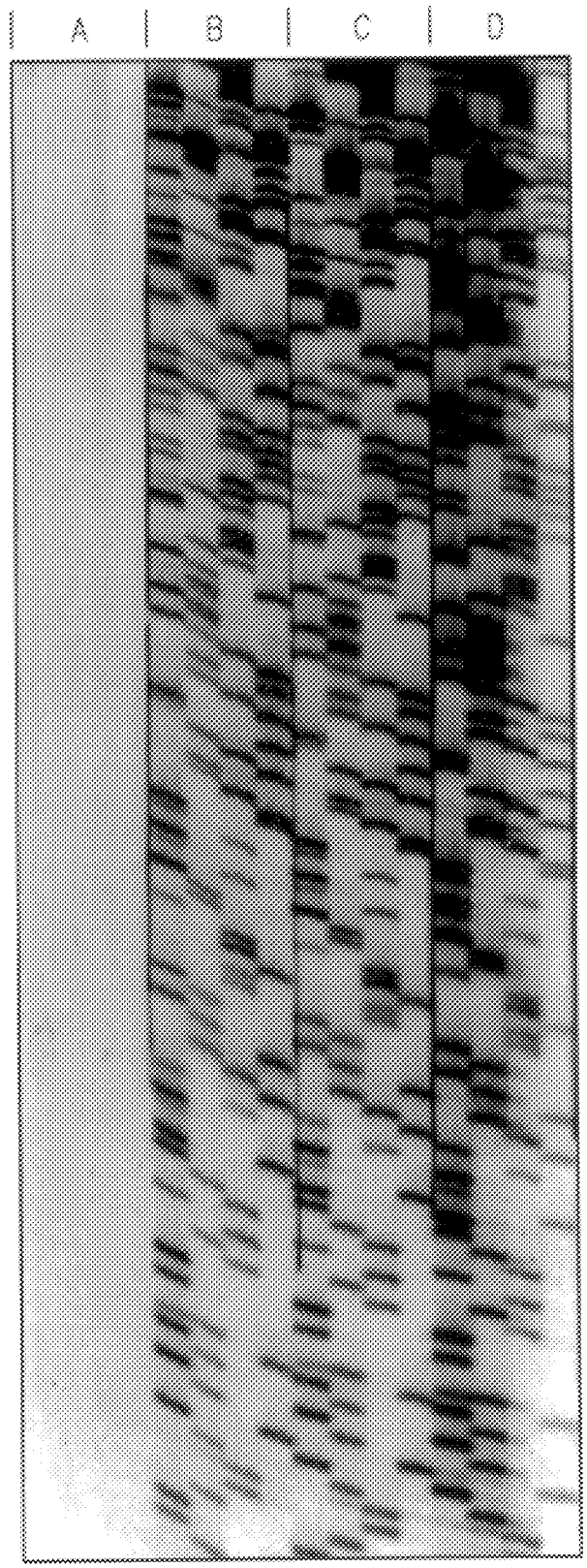
FIG. 6 illustrates the sequencing gel results of sequencing pBluescript® plasmid with reverse transcriptase using a 16mer oligonucleotide primer produced as described in Example 7 by ligation of degenerate oligonucleotide compositions. Sequencing results are shown using the primers in primer set 7 in 16 consecutive lanes (A–D), where the four lanes labeled A illustrate a negative control by sequencing with a reaction product produced from a mock-ligation reaction of degenerate oligonucleotide compositions 7An, 7Bn, 7Cn and 7Dn without ligase added to the ligation reaction, the four lanes labeled B illustrate sequencing with a positive control chemically synthesized 16mer primer (oligonucleotide 7), the four lanes labeled C illustrate sequencing with the ligation reaction product from degenerate oligonucleotide compositions 7An, 7Bn, 7Cn and 7Dn with ligase added to the ligation reaction, and the four lanes labeled D illustrate sequencing as in the C lanes, except the primer used was formed by ligation of the non-degenerate oligonucleotides 7A, 7B, 7C and 7D.

The resulting RT sequencing reactions analysed on a sequencing gel are shown in FIG. 6. The 16mer degenerate oligonucleotide (7n) ligation reaction product in unpurified form (i.e., used directly from the ligation reaction admixture) specifically primed a unique sequence ladder using the pBluescript® plasmid template forming a clean and readable sequencing 5 ladder, as shown in the B lanes of FIG. 6. The sequence ladder produced by a chemically synthesized 16mer (oligonucleotide 7) primer (shown in the C lanes) or the ladder produced by the non-degenerate ligation reaction product (primer set 7A–D; shown in the D lanes) was indistinguishable from the ladder formed by the degenerate oligonucleotide ligation reaction product, indicating that primer produced by the present methods with degenerate oligonucleotides efficiently primes sequencing reactions. In the absence of ligase, no sequence ladder is seen (shown in the A lanes) indicating that non-ligated 8mers do not significantly prime a sequencing reaction under the conditions utilized.

8. Modified $T_7$ DNA Polymerase Sequencing Using a Degenerate Oligonucleotide Ligation Reaction Product as Primer The oligonucleotide in the ligation reaction product formed by using degenerate oligonucleotide set 7n was used to prime a DNA sequencing reaction, in a sequencing format that uses a modified $T_7$ DNA polymerase that exhibits reduces 3'to 5' exonuclease activity. The polymerase used in this case is referred to as Sequenase. To that end, a 10 ul Sequenase sequencing reaction admixture was prepared by first admixing the following: 2 ul 5X Sequenase buffer (40 mM Tris-HCl, pH 7.5, 20 mM KCl, 50 mM NaCl), 3 ug denatured double-stranded pBluescript® plasmid DNA, 2 ul containing ligation reaction product from degenerate oligonucleotide primer set 7n or 5 ng of 16mer control oligonucleotide 7 (SEQ ID NO 6) and sufficient distilled water to bring the volume to 10 ul. This first admixture was incubated for 2–3 min at 50° C. Thereafter, 2.5 ul of label mix was added containing 5 uCi $\alpha^{33}$P-dATP (1332 Ci/mmole; 10 uCi/ml; New England Nuclear), 1.5 uM dCTP, 1.5 uM dGTP, 1.5 uM dTTP and 5 units Sequenase (U.S. Biochemicals), to form a Sequenase labeling reaction admixture. The admixture was incubated 3–5 min at 50° C. to form labeled reaction product, and then 2.5 ul of the labeled reaction product was transferred to a fresh prewarmed (37° C.) tube containing 2.5 ul of one of the four ddNTP mix (Example 4) and 0.5 units of Sequenase diluted in enzyme dilution buffer (Example 4) to form a Sequenase sequencing reaction admixture. The Sequenase sequencing reaction admixture was incubated 3–5 min at 37° C., and then 4 ul of stop solution (Example 4) was added to the incubated admixture. Two ul of the resulting Sequenase sequencing reaction admixture were loaded onto and electrophoresed on a sequencing gel as described in Example 3 for cycle sequencing.

Oligonucleotide primer sets 6n and 8n were similarly prepared from the oligonucleotides shown in Table 2, ligated as in Example 5 and used in Sequenase sequencing as described above for primer set 7n, and the sequencing results analyzed on sequencing gels.

Figure 7:
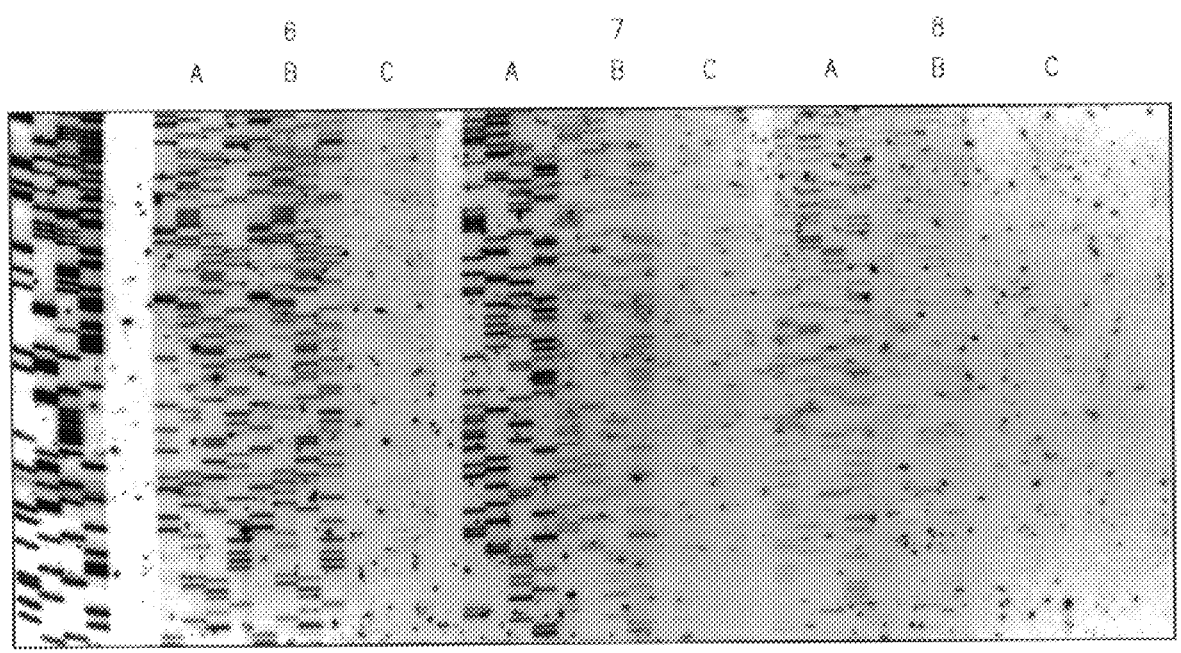
FIG. 7 illustrates the sequencing gel results of sequencing pBluescript® plasmid with Sequenase using a 16mer oligonucleotide primer produced as described in Example 8 by ligation of degenerate oligonucleotide compositions. Sequencing results are shown using the same format and with the same primers as described in the legend to FIG. 5, except that the nucleotide sequences were produced using Sequenase sequencing.

The resulting Sequenase sequencing reactions analyzed on a sequencing gel are shown in FIG. 7.

The results show that the sequencing ladder (four lanes corresponding to A, T, G and C) produced by three different degenerate oligonucleotide primers (shown in the B lanes for primer sets 6n, 7n or 8n) upon ligation according to the present methods is essentially indistinguishable from the sequencing ladder produced by using a synthetic 16mer primer (shown in the A lanes for oligonucleotides 6, 7 or 8), indicating that the primer produced by the present methods efficiently primes a Sequenase sequencing reaction without undesirable interfering reaction. In the absence of added ligase (shown in the C lanes), no sequencing ladder is seen indicating that the non-ligated 8mers of the degenerate oligonucleotide composition do not significantly prime the Sequenase sequencing reaction. The random specs present on the illustrated gel is an artifact of static electricity during the film development process, can generally be prevented, and is not to be considered a limitation in resolution for the present sequencing method.

The foregoing specification, including the specific embodiments and examples, is illustrative of the present invention and is not intended to limit the invention in any way. It will be apparent to those skilled in the art that numerous variations and modifications to the above-described embodiments of the invention will be possible without departing from the spirit and scope of the invention. It is intended that the following claims be interpreted to embrace all such variations and modifications.

What is claimed is:

1. An oligonucleotide library useful for producing an oligonucleotide of preselected sequence comprising a plurality of oligonucleotide members comprising one or more oligonucleotide species and having the compositional formula $(X)_a(N)_b$; wherein X represents a non-degenerate nucleotide base and N represents a degenerate nucleotide base; "a" represents the number of non-degenerate nucleotide positions and is from 3 to 8; "b" represents the number of degenerate nucleotide positions and is from 0 to 4 but not greater than "a"; and wherein each of said oligonucleotide species is capable of forming a hybridization complex with at least one other of said oligonucleotide species in said library, said hybridization complex having at least one unpaired nucleotide base overhang such that a single ligation event of said hybridization complex with another hybridization complex derived from said library having a complementary unpaired nucleotide base overhang produces a ligation reaction product comprising greater than 12 contiguous nucleotide base pairs.

2. The oligonucleotide library of claim 1 wherein said hybridization complexes comprise at least one nucleotide.

3. The oligonucleotide library of claim 1 wherein said library contains no greater than 60,000 different oligonucleotide species.

4. The oligonucleotide library of claim 1 wherein said compositional formula is selected from the group consisting of $(X)_5(N)_1$, $(X)_4(N)_2$, $(X)_6(N)_1$, $(X)_5(N)_2$ and $(X)_6(N)_2$.

5. The oligonucleotide library of claim 4 wherein said compositional formula is $(X)_6(N)_2$.

6. The oligonucleotide library of claim 5 wherein said compositional formula is 5'-XXNXXNXX-3'.

7. The oligonucleotide library of claim 1 wherein X and N are the nucleotide bases A, T, G, C, or analogs thereof.

8. The oligonucleotide library of claim 5 wherein said library has 4,096 different oligonucleotide members.

9. The oligonucleotide library of claim 1 wherein each of said oligonucleotide members have a 5' terminal phosphate.

10. A kit useful for producing an oligonucleotide of preselected sequence comprising, in separate enclosures, one or more libraries according to claims 1, 2, 3, 4, 5, 6 or 7, and a suitable ligase or polymerase.

11. A method for producing an oligonucleotide of preselected nucleotide sequence comprising the steps of:

a) selecting at least one oligonucleotide member from a library according to claims 1, 2, 3, 4, 5, 6 or 7;

b) hybridizing in an aqueous ligation buffer the oligonucleotide member(s) selected in step (a) having a preselected nucleotide sequence and capable of hybridizing to form a ligation reaction substrate; and c) ligating said ligation reaction substrate to form a ligation reaction product containing said oligonucleotide of preselected nucleotide sequence.

12. The method of claim 11 wherein four different oligonucleotide members are selected in step (a).

13. The method of claim 11 wherein six different oligonucleotide members are selected in step (a).

14. An oligonucleotide composition useful for producing an oligonucleotide of preselected sequence comprising a plurality of different oligonucleotide species, each having the compositional formula $(X)_a(N)_b$, and having a length of from 5 to 12 nucleotides; wherein X represents a non-degenerate nucleotide base and N represents a degenerate nucleotide base; "a" represents the number of non-degenerate nucleotide positions and is from 3 to 8; "b" represents the number of degenerate nucleotide positions and is from 1 to 4 but not greater than "a".

15. The oligonucleotide composition of claim 14 wherein said compositional formula is selected from the group consisting of $(X)_5(N)_1$, $(X)_4(N)_2$, $(X)_6(N)_1$, $(X)_5(N)_2$ and $(X)_6(N)_2$.

16. The oligonucleotide composition of claim 15 wherein said compositional formula is $(X)_6(N)_2$.

17. The oligonucleotide composition of claim 16 wherein said compositional formula is 5'-XXNXXNXX-3'.

18. The oligonucleotide composition of claim 14 wherein said composition contains all possible combinations of nucleotide sequences at positions designated by an N.

19. The oligonucleotide composition of claim 14 wherein X and N are the nucleotide bases A, T, G, C, or analogs thereof.

20. The oligonucleotide composition of claim 14 wherein each of said oligonucleotides have a 5' terminal phosphate.

* * * * *

(12) EX PARTE REEXAMINATION CERTIFICATE (9451st)
United States Patent
Sorge et al.

(10) Number: US 5,858,731 C1
(45) Certificate Issued: Dec. 20, 2012

(54) OLIGONUCLEOTIDE LIBRARIES USEFUL FOR PRODUCING PRIMERS

(75) Inventors: Joseph A. Sorge, San Diego, CA (US); Daniel Davis Shoemaker, Stanford, CA (US)

(73) Assignee: Stratagene, La Jolla, CA (US)

Reexamination Request:
No. 90/011,936, Sep. 29, 2011

Reexamination Certificate for:
Patent No.: 5,858,731
Issued: Jan. 12, 1999
Appl. No.: 08/313,232
Filed: Feb. 20, 1996

Related U.S. Application Data

(63) Continuation-in-part of application No. 07/863,412, filed on Apr. 3, 1992, now abandoned, which is a continuation-in-part of application No. 07/765,694, filed on Sep. 25, 1991, now abandoned, and a continuation-in-part of application No. 07/697,936, filed on May 8, 1991, now Pat. No. 5,599,921.

(51) Int. Cl.
*B01J 19/00* (2006.01)
*C12Q 1/68* (2006.01)
*C07H 21/00* (2006.01)
*C12N 15/10* (2006.01)

(52) U.S. Cl. .................. 435/91.1; 536/24.3; 536/24.33; 536/25.3

(58) Field of Classification Search ........................ None
See application file for complete search history.

(56) References Cited

To view the complete listing of prior art documents cited during the proceeding for Reexamination Control Number 90/011,936, please refer to the USPTO's public Patent Application Information Retrieval (PAIR) system under the Display References tab.

*Primary Examiner* — Johnny F Railey

(57) ABSTRACT

An oligonucleotide library is described that is1 useful for producing an oligonucleotide of preselected sequence comprising a plurality of oligonucleotide members comprising one or more oligonucleotide species and having the compositional formula $(X)_a(N)_b$; wherein X represents a non-degenerate nucleotide base and N represents a degenerate nucleotide base; "a" represents the number of non-degenerate nucleotide positions and is from 3 to 8; "b" represents the number of degenerate nucleotide positions and is from 0 to 4 but not greater that "a"; and wherein each of the oligonucleotide species is capable of forming a hybridization complex with at least one other of the oligonucleotide species in the library such that a single ligation event of the hybridization complex with another hybridization complex derived from the library produces a ligation reaction product comprising greater than 12 contiguous nucleotide base pairs.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 14 and 18 are cancelled.

Claims 1-13, 15-17, 19 and 20 were not reexamined.

\* \* \* \* \*